United States Patent [19]

Nolan et al.

[11] Patent Number: 6,087,128
[45] Date of Patent: Jul. 11, 2000

[54] DNA ENCODING AN AVIAN *E. COLI* ISS

[75] Inventors: Lisa K. Nolan; Shelley M. Horne, both of Fargo, N. Dak.

[73] Assignee: NDSU Research Foundation, Fargo, N. Dak.

[21] Appl. No.: 09/023,221

[22] Filed: Feb. 12, 1998

[51] Int. Cl.[7] ........................... C12N 15/31; C12N 15/70; C12N 15/79; C07K 14/245

[52] U.S. Cl. .................... 435/69.3; 435/69.1; 435/320.1; 536/23.7

[58] Field of Search ....................... 536/23.7; 435/320.1, 435/69.1, 69.3

[56] References Cited

U.S. PATENT DOCUMENTS

| | | | |
|---|---|---|---|
| 3,842,067 | 10/1974 | Sarantakis | 530/311 |
| 3,862,925 | 1/1975 | Sarantakis et al. | 530/311 |
| 3,972,859 | 8/1976 | Fujino et al. | 530/313 |
| 4,105,602 | 8/1978 | Colescott et al. | 524/577 |
| 4,341,761 | 7/1982 | Ganfield et al. | 424/85.6 |
| 4,342,832 | 8/1982 | Goeddel et al. | 435/91.41 |
| 4,366,246 | 12/1982 | Riggs | 435/69.8 |
| 4,399,121 | 8/1983 | Albarella et al. | 530/363 |
| 4,411,994 | 10/1983 | Gilbert et al. | 435/69.7 |
| 4,418,149 | 11/1983 | Ptnashe et al. | 435/252.33 |
| 4,425,437 | 1/1984 | Riggs | 435/320.1 |
| 4,427,783 | 1/1984 | Newmann et al. | 436/542 |
| 4,428,941 | 1/1984 | Galibert et al. | 514/2 |
| 4,431,739 | 2/1984 | Riggs | 435/252.33 |
| 4,431,740 | 2/1984 | Bell et al. | 435/252.33 |
| 4,436,815 | 3/1984 | Hershberger et al. | 435/34 |
| 4,440,859 | 4/1984 | Rutter et al. | 435/91.41 |
| 4,444,887 | 4/1984 | Hoffman | 435/373 |
| 4,466,917 | 8/1984 | Nussenzweig et al. | 530/350 |
| 4,472,500 | 9/1984 | Milstein et al. | 435/70.21 |
| 4,491,632 | 1/1985 | Wands et al. | 435/339 |
| 4,493,890 | 1/1985 | Morris | 435/7.7 |
| 4,683,195 | 7/1987 | Mullis et al. | 435/6 |
| 4,757,048 | 7/1988 | Lewicki et al. | 514/11 |
| 5,001,230 | 3/1991 | Brown et al. | 536/23.5 |

FOREIGN PATENT DOCUMENTS

| | | |
|---|---|---|
| 103395 | 3/1984 | European Pat. Off. . |
| 116201 | 8/1984 | European Pat. Off. . |
| 120551 | 10/1984 | European Pat. Off. . |
| 164556 | 12/1985 | European Pat. Off. . |
| 2007675 | 5/1979 | United Kingdom . |
| 2008123 | 5/1979 | United Kingdom . |
| 2121054 | 12/1983 | United Kingdom . |
| WO 93/02556 | 2/1993 | WIPO . |

OTHER PUBLICATIONS

F. R. Blattner et al., "The Complete Genome Sequence of *Escherichia coli* K–12," *Science*, 277: 1453–1462 (1997).

(Poster) J. O. Ebert et al., "Role of iss in the Complement Resistance and Virulence of an Avian *Escherichia coli*," North Dakota Science, Engineering, and Mathematics Poster Session, North Dakota Epscor, North Dakota State University, Fargo, ND (Jul. 30,1997).

Title page, table of contents, and abstract PP23 for L. K. Nolan et al., "Contribution of iss to the Virulence of an Avian *Escherichia coli*," Department of Veterinary and Microbiological Sciences, North Dakota State University, Fargo, ND, Presented at 134th Annual Convention of the American Veterinary Medical Association, Reno, NV (Jul. 19–24, 1997).

(Poster) L. K. Nolan et al., "Contribution of iss to the Virulence of an Avian *Escherichia coli*," Department of Veterinary and Microbiological Sciences, North Dakota State University, Fargo, ND, Presented at 134th Annual Convention of the American Veterinary Medical Association, Reno, NV (Jul. 19–24, 1997).

(Poster) S. J. Pfaff–McDonough et al., "Markers of Complement Resistance and Virulence Among Avian *Escherichia coli* Isolates," Department of Veterinary and Microbiological Sciences, North Dakota State University, Fargo, ND, Presented at 134th Annual Convention of the American Veterinary Medical Association, Reno, NV(Jul. 19–24, 1997).

(Poster) P.R. Topp et al., "Detection of iss in Avian *E. coli*," North Dakota Science, Engineering, and Mathematics Poster Session, North Dakota Epscor, North Dakota State University, Fargo, ND (Jul. 30, 1997).

(Abstract) P. R. Topp et al., "Detection of iss in Avian *E. coli*," North Dakota Science, Engineering, and Mathematics Poster Session, North Dakota Epscor, North Dakota State University, Fargo, ND (Jul. 30, 1997).

B. Abdallah et al., "Non–Viral Gene Transfer: Applications in Developmental Biology and Gene Therapy," *Biol. Cell* 85(1) 1–7 (1995).

J. P. Adelman et al., "In Vitro Deletional Mutagenesis for Bacterial Production of the 20,000–Dalton Form of Human Pituitary Growth Hormone," *DNA* 2: 183–179 (1983).

P.J. Barr et al. "7–Deaza–2'–Deoxyguanosine–5'–Triphosphate: Enhanced Resolution in M13 Dideoxy Sequencing," *Biotechniques*, 4: 428–432 (1986).

H. Baumann et al., "Dexamethasone Regulates the Program of Secretory Glycoprotein Synthesis in Hepatoma Tissue Culture Cells," *J. Cell Biol.*, 85:1–8 (1980).

E. Beck et al., "Nucleotide Sequence of the Gene ompA Coding the Outer Membrane Protein II* of *Escherichia coli* K–12," *Nuc. Acids Res.*, 8:3011–3024 (1980).

J. R. Broach et al., "Construction of High Copy Yeast Vectors Using 2–μm Circle Sequences," *Meth. Enz.*, 101:307–325 (1983).

L. A. Carpino et al., "The 9–Fluorenylmethoxycarbonyl Amino–Protecting Group,"*J. Org. Chem.*, 37:3404–3409 (1972).

(List continued on next page.)

*Primary Examiner*—Johnny F. Railey, II

[57] ABSTRACT

A nucleic acid sequence encoding an avian *E. coli* iss gene and an Iss polypeptide encoded thereby are disclosed. Methods for detecting and using such sequences are also provided as are immunogenic compositions and vaccines.

19 Claims, 5 Drawing Sheets

OTHER PUBLICATIONS

Chang et al.., "Solid–Phase Peptide Synthesis Using Mild Base Cleavage of Nα–Fluorenylmethyloxycaronylamino Acids, Exemplified by a Synthesis of Dihydrosomatostatin," *Int. J. Peat. Pro. Res.*, 11:246–249 (1978).

D. B. Clewell et al., "Supercoiled Circular DNA–Prtein Complex in *Escherichia Coli*: Purification and Induced Conversion to an Open Circular DNA Form," *Proc. Natl. Acad. Sci. USA*, 62:1159–1166 (1969).

D. B. Clewell, "Nature of Col $E_1$ Plasmid Replication in *Escherichia Coli* in the Presence of Chloramphenicol," *J. Bacteriol.*, 110:667–676 (1972).

S. N. Cohen et al., "Nonchromosomal Antibiotic Resistance in Bacteria: Genetic Transformation of *Escherichia coli* by R–Factor DNA," *Proc. Natl. Acad. Sci. USA*, 69:2110–2114 (1972).

J. J. Donnelly et al., "Effective Efficacy of Intramuscular Immunization with Naked DNA," *Ann. N.Y. Acad. Sci.* 772:40–46 (1995).

M. D. Edge et al., "Total Synthesis of a Human Leukocyte Interferon Gene," *Nature*, 292:756–762 (1981).

W. Fiers et al. "Complete Nucleotide Sequence of SV40 DNA," *Nature*, 273:113–120 (1978).

L. Gilson et al., "Four Plasmid Genes Are Required for Colicin V Synthesis, Export; and Immunity," *J. Bacteriol.* 169:2466–2470 (1987).

D. V. Goeddel et al. "Synthesis of Human Fibroblast Interferon by *E. Coli*," *Nucleic Acids Res.*, 8: 4057–4074 (1980).

F. L. Graham et al., "A New Technique for the Assay of Infectivity of Human Adenovirus 5 DNA," *Virology*, 52:546 (1973).

M. Grunstein et al., "Colony Hybridization: A Method for the Isolation of Cloned DNAs that Contain a Specific Gene," *Proc. Natl. Acad. Sci.* (USA), 72:3961–3965 (1975).

C.L. Gyles, Chapter 15 of *Pathogenesis of Bacterial Infections in Animals, Second Ed.*, (C.L. Gyles et al., Eds.) Iowa State University Press, Ames, IA, pp. 164–187, (1993).

B. Hess et al. "Cooperation of Glycolytic Enzymes," *J. Adv. Enzyme Reg*, 7:149–167 (1968).

A. Hinnen et al. "Transformation of Yeast," *Proc. Natl. Acad. Sci.*, 75:1929–1933 (1978).

P. H. Hiss, Jr., "A Contribution to the Physiological Differentiation of Pneumococcus and Streptococcus, and to Methods of Staining Capsules," *J. Exp. Med.* 6:317–345 (1905).

R. A. Hitzeman et al. "Isolation and Characterization of the Yeast 3–Phosphoglycerokinase Gene (PGK) by an Immunological Screening Technique," *J. Biol. Chem.*, 255: 12073–12080 (1980).

M. J. Holland et al. "Isolation and Identification of Yeast Messenger Ribonucleic Acids Coding for Enolase, Glyceraldehyde–3–phosphate Dehydrogenase, and Phosphoglycerate Kinase," *Biochemistry*, 17:4900–4907 (1978).

M. J. Holland et al. "The Primary Structures of Two Yeast Enolase Genes," *J. Biol Chem.*, 256:1385–1395 (1981).

E. Jay et al., "Chemical Synthesis of a Biologically Active Gene for Human Immune Interferon– γ"*J. Biol. Chem.* 259:6311–6317 (1984).

T. J. Kottom et al., "Further Characterization of a Complement–Sensitive Mutant of a Virulent Avian *Escherichia coli* Isolate," *Avian Dis.*, 41: 817–823(1997).

M. D. Lee et al., "Comparison of a Quantitative Microtiter Method, a Quantitative Automated Method, and the Plate–Count Method for Determining Microbial Complement Resistance," *Avian Dis.*, 35: 892–896 (1991).

V.A. Luckow et al., "High Level Expression of Nonfused Foreign Genes with *Autographa californica* Nuclear Polyhedrosis Virus Expression Vecors," *Virology*, 170:31–39 (1989).

J. Marmur, "A Procedure for the Isolation of Deoxyribonucleic Acid from Micro–organisms," *J. Mo. Biol.*, 3:208–218 (1961).

J. P. Mather et al., "Culture of Testicular Cells in Hormone–Supplemented Serum–Free Medium," *Annals N.Y. Acad. Sci.*, 383:44–68 (1982).

A. M. Maxam et al. "Sequencing End–Labeled DNA with Base–Specific Chemical Cleavages," *Methods in Enzymology*, 65:499–560 (1980).

A. E. Maxwell, *Analyzing Qualitative Data*, Methuen Co., London (1961).

R. B. Merrifield, "Solid Phase Peptide Synthesis. I. The Synthesis of a Tetrapeptide," *J. Am. Chem. Soc.*, 85:2149–2154 (1963).

J. Messing et al. "A System for Shotgun DNA Sequencing," *Nucleic Acids Res.*, 9:309–321 (1981).

B. H. Minshew et al., "Association of Hemolysin Production, Hemagglutination of Human Erthrocytes, and Virulence for Chicken Embryos of Extraintestinal *Escherichia coli* Isolates," *Infect Immun.* 20:50–54 (1978).

K. Molling, "Naked DNA for Vaccine or Therapy," *J. Mol. Med.* 75:242–246 (1997).

K. Mullis et al., "Specific Enzymatic Amplification of DNA In Vitro: The Polymerase Chain Reaction," *Cold Harbor Symp. Quant. Biol.*, 51:263 (1987).

K. P. Nambiar et al., "Total Synthesis and Cloning of a Gene Coding for the Ribonclease S Protein," *Science* 223:1299–1301 (1984).

D. M. Pardoll et al., "Exposing the Immunology of Naked DNA Vaccines," *Immunity* 3:165–169 (1995).

Pharmacia Biotech, GST Gene Fusion System, Third Edition, Revision 1 (product No. 18–1123–20), Bulk GST Purification Module (product No. 27–4570–01), Redipack GST Purification Module (product No. 27–4570–02) (1997).

Sambrook et al., "Appendix D: Codons and Amino Acids," *Molecular Cloning: A Laboratory Manual*, p. D1 (1989).

F. Sanger et al. "DNA Sequencing with Chain–Terminating Inhibitors," *Proc. Natl. Acad. Sci. USA*, 74:5463–5467 (1977).

F. Sanger et al., "Nucleotide Sequence of Bacteriophage λ DNA," *J. Mol. Biol.*, 162:729–773 (1982).

H. Shimatake et al. "Purified λ Regulatory Protein cII Positively Activates Promoters for Lysogenic Development," *Nature*, 292:128–132 (1981).

G. Simmons et al., "Potent Inhibition of HIV–1 Infectivity in Macrophages and Lymphocytes by a Novel CCR5 Antagonist," *Science* 276:276–279 (1997).

F. K. Stevenson et al., "Idiotypic DNA Vacines Against B–Cell Lymphoma," *Immunol. Rev.* 145:211–228 (1995).

B. D. Warner et al., "Laboratory Methods: Construction and Evaluation of an Instrument for the Automated Synthesis of Oligodeoxyribonucleotides," *DNA*, 3:401–411 (1984).

N. S. Yang et al., "Developing Particle–Mediated Gene–Transfer Technology for Research into Gene Therapy of Cancer," *Mol. Med. Today* 2:476–481 (1996).

M. J. Zoller et al., "Oligonucleotide–Directed Mutagenesis Using M13–Derived Vectors: An Efficient and General Procedure for the Production of Point Mutations in Any Fragment of DNA," *Nucleic Acids Res.*, 10:6487–6500 (1982).

Agëro, M., et al., "Relative Contribution of ColV Plasmid and K1 Antigen to the Pathogenicity of *Escherichia coli*", *Infection and Immunity*, 40, 359–368, (1983).

Arp, L., et al., "Piliation, Hemagglutination, Motility, and Generation Time of *Escherichia coli*", *Avian Diseases*, 24, 153–161, (1980).

Barondess, J., et al., "A Bacterial Virulence Determinant Encoded by Lysogenic Coliphage λ", *Nature*, 346, 871–874, (1990).

Barondess, J., et al., "bor Gene of Phage λ, Involved in Serum Resistance, Encodes a Widely Conserved Outer Membrane Lipoprotein", *J. Bacteriology*, 177, 1247–1253, (1995).

Binns, M., et al., "Cloned Fragments of the Plasmid ColV, I–K94 Specifying Virulence and Serum Resistance", *Nature*, 279, 778–781, (1979).

Binns, M., et al., "Further Characterization of Complement Resistance Conferred on *Escherichia coli* by the Plasmid Genes traT of R100 and iss of ColV, I–K94", *Infection and Immunity*, 35, 654–659, (1982).

Butler, D., et al., "Ch. 4: Diarrhoea and Dysentery in Calves", In: *Escherichia Coli in Domestic Animals and Humans*, C.L. Gyles, ed., CAB International, 91–116, (1994).

Chuba, P., et al., "Cloning and DNA Sequence of Plasmid Determinant iss, Coding for Increased Serum Survival and Surface Exclusion, which has Homology with Lambda DNA", *Molecular & General Genetics*, 216, 287–292, (1989).

Chuba, P., et al., "Contributions of traT and iss genes to the Serum Resistance Phenotype of plasmid Col V2-K94", *FEMS Microbiology Letters*, 37, 135–140, (1986).

Cloud, S., et al., "In Vitro and In Vivo Characterization of Avian *Escherichia coli*. I. Serotypes, Metabolic Activity, and Antibiotic Sensitivity", *Avian Diseases*, 29, 1084–1093, (1985).

Cross, A., et al., "The Relative Role of Lipopolysaccharide and Capsule in the Virulence of *E. Coli*", In: *Bacteria, Complement and the Phagocytic Cell*, 24, F. C. Cabello, et al., eds., Springer–Verlag, Berlin, 319–334, (1988).

Fernandez–Beros, M., et al., "Virulence–Related Genes in ColV Plasmids of *Escherichia coli* Isolated from Human Blood and Intestines", *J. Clinical Microbiology*, 28, 742–746, (1990).

Goldman, R., et al., "Serum–Resistant Mutants of *Escherichia coli* 0111 Contain Increased Lipopolysaccharide, Lack an O Antigen–Containing Capsule, and Cover More of Their Lipid A Core with O Antigen", *J. Bacteriology*, 159, 877–882, (1984).

Gross, W., In: *Disease of Poultry*, 8th Edition, M.S. Hofstad, et al., eds., Iowa State University Press, Iowa., 270–278, (1984).

Ike, K., et al., "Serum Resistance and Aerobactin Iron Uptake in Avian *Escherichia coli* Mediated by Conjugative 100–Megadalton Plasmid", *J. Verterinary Medical Science*, 54, 1091–1098, (1992).

Mims, C., *The Pathogenesis of Infectious Disease*, 2nd Edition, Academic Press, New York, (1982), Preface and Table of Contents only.

Moll, A., et al., "Plasmid–Determined Resistance to Serum Bactericidal Activity: a Major Outer Membrane Protein, the traT Gene Product, Is Responsible for Plasmid–Specified Serum Resistance in *Escherichia coli*", *Infection and Immunity*, 28, 359–367, (1980).

Moll, A., et al., "Rapid Assay for the Determination of Bacterial Resistance to the Lethal Activity of Serum", *FEMS Microbiology Letters*, 6, 273–279, (1979).

Montenegro, M., et al., "traT Gene Sequences, Serum Resistance and Pathogenicity–related Factors in Clinical Isolates of *Escherichia coli* and Other Gram–negative Bacteria", *J. General Microbiology*, 131, 1511–1521, (1985).

Naveh, M., et al., "Adherence Pili in Avian Strains of *Escherichia coli*: Effect on Pathogenecity", *Avian Diseases*, 28, 651–661, (1984).

Nolan, L., et al., "Characterization of an Avirulent Mutant of a Virulent *Escherichia coli* Isolate", *Avian Diseases*, 38, 146–150, (1994).

Nolan, L., et al., "Comparison of a Complement Resistance Test, a Chicken Embryo Lethality Test, and the Chicken Lethality Test for Determining Virulence of Avian *Escherichia coli*", *Avian Diseases*, 36, 395–397, (1992).

Nolan, L., et al., "Transposon Mutagenesis used to Study the Role of Comlement Resistance in the Virulence of an Avian *Escherichia coli* Isolate", *Avian Diseases*, 36, 398–402, (1992).

Pluschke, G., et al., "Role of the Capsule and the O Antigen in Resistance of 018:K1 *Escherichia coli* to Complement–Mediated Killing", *Infection and Immunity*, 42, 907–913, (1983).

Provence, D., et al., "Isolation and Characterization of a Gene Involved in Hemagglutination by an Avian Pathogenic *Escherichia coli* Strain", *Infection and Immunity*, 62, 1369–1380, (1994).

Provence, D., et al., "Role of crl in Avian Pathogenic *Escherichia coli*: a Knockout Mutation of crl Does Not Affect Hemagglutination Activity, Fibronectin Binding, or Curli Production", *Infection and Immunity*, 60, 4460–4467, (1992).

Rosenberger, J., et al., "In Vitro and In Vivo Characterization of Avian *Escherichia coli*. II. Factors Assoicated with Pathogenicity", *Avian Diseases*, 29, 1094–1107, (1985).

Russo, T., et al., "TnphoA–Mediated Disruption of K54 Capsular Polysaccjaride Genes in *Escherichia coli* Confers Serum Sensitivity", *Infection and Immunity*, 61, 3578–3582, (1993).

Sussman, M.,ed. The Virulence of *Escherichia coli*, Academic Press, London, (1985), Preface and Table of Contents only.

Taylor, P., "Bactericidal and Bacteriolytic Activity of Serum Against Gram–Negative Bacteria", *Microbiological Reviews*, 47, 46–83, (1983).

Timmis, K., et al., "Surface Components of *Escherichia coli* That Mediate Resistance to the Bactericidal Activities of Serum and Phagocytes", *Current Topics in Microbiology and Immunology*, 118, 197–218, (1985).

Vidotto, M., et al., "Virulence Factors of Avian *Escherichia coli*", *Avian Diseases*, 34, 531–538, (1990).

Waters, V., et al., "Colicin V Virulence Plasmids", *Microbiological Reviews*, 55, 437–450, (1991).

Weiser, J., et al., "Outer Membrane Protein A (OmpA) Contributes to Serum Resistance and Pathogenicity of *Escherichia coli* K–1", *Infection and Immunity*, 59, 2252–2258, (1991).

Wooley, R., et al., "Relationship of Complement Resistance and Selected Virulence Factors in Pathogenic Avian *Escherichia coli*", *Avian Diseases*, 36, 679–684, (1992).

Ferrazza et al., J. Bacter. 144(1):149–158 (1980).

Crowl et al., Gene 38:31–38 (1985).

Boswell et al., in *Computational Molecular Biology: Sources and Methods for Sequence Analysis*, Arthur M. Lesk, ed., Oxford University Press, New York, 1988, pp. 161–178.

FIGURE 1

```
Eciss   ATGCAGGATAATAAGATGAAAAAAATGTTATTTTCTGCCGCTCTGGCAATGCTTATTACA    60
        ||||||||||||||||||||||||||||||||||||||||||||||||||||||||||||
102iss  ATGCAGGATAATAAGATGAAAAAAATGTTATTTTCTGCCGCTCTGGCAATGCTTATTACA    60
         ||||  |   |||||||||||  ||  |   ||  ||  ||||||   ||||||||||||
lambor  ATCGGGAATAACACCATGAAAAAAATGCTACTCGCTACTGCGCTGGCCCTGCTTATTACA    60

Eciss   GGATGTGCTCAACAAACGTTTACTGTTGGAAACAAACCGACAGCAGTAACACCAAAGGAA   120
        ||||||||||||||||||||||||||||||||||||||||||||||||||||||||||||
102iss  GGATGTGCTCAACAAACGTTTACTGTTGGAAACAAACCGACAGCAGTAACACCAAAGGAA   120
        ||||||||||||| |||||||||||  |||||||||||  ||||||| |||||||||||||
lambor  GGATGTGCTCAACAGACGTTTACTGTTCAAAACAAACCGGCAGCAGTAGCACCAAAGGAA   120

Eciss   ACCATCACTCATCATTTCTTCGTTTCCCCAATTGGAC-AGAGAAAACTGTTGATGCAGCC   179
        |||||||||||||||||||||||||||    ||||||||   |||||||||||||||||||
102iss  ACCATCACTCATCATTTCTTCGTTTCGGGAATTGGACAAGAGAAAACTGTTGATGCAGCC   180
        |||||||  ||||||||||||||||  ||||||||  |  |||||||||||  ||||||||
lambor  ACCATCACCCATCATTTCTTCGTTTCTGGAATTGGGCAGAAGAAAACTGTCGATGCAGCC   180

Eciss   AAAATTTGTTGGCGGTGCAGAAAATGTTGTTAAAACAGAAACTCAGCAAACATTCGTAAA   239
        |||||||  ||||||||||||||||||||||||||||||||||||||||||||||||||||
102iss  AAAATTTG-TGGCGGTGCAGAAAATGTTGTTAAAACAGAAACTCAGCAAACATTCGTAAA   239
        |||||||  ||||||  ||||||||||||||||||||||||  |||||||||||||||||
lambor  AAAATTTG-TGGCGGCGCAGAAAATGTTGTTAAAACAGAAACCCAGCAAACATTCGTAAA   239

Eciss   TGCATTGCCCGGTTTTATCACTTTTGGCATCTATACTCCGCGGGAAACCCGTGTATATTG   299
         | |||||  ||||||||||||||||||||||||||||||| ||||  ||||  ||||||||
102iss  TGGATTGCTCGGTTTTATCACTTTTGGCATCTATACTCCGCTGGAAGCCCGGGTATATTG   299
        ||||||||||||||||||||| |||||  |||||  |||||||||||||||  || ||  |||||
lambor  TGGATTGCTCGGTTTTATTACTTTAGGCATTTATACTCCGCTGGAAGCGCGTGTGTATTG   299

Eciss   CTCACAATAG                                                    309
        ||||||||||
102iss  CTCACAATAG                                                    309
        |||||||||
lambor  CTCACAATAA                                                    309
```

FIGURE 2

```
Iss_Ec   MQDNKMKKMLFSAALAMLITGCAQQTFTVGNKPTAVTPKETITHHFFVSPIGQRKLLMQP    60
         ||||||||||||||||||||||||||||||||||||||||:|||||||||  |||  |  : ::
102Iss   MQDNKMKKMLFSAALAMLITGCAQQTFTVGNKPTAVTPKETITHHFFVSGIGQEKTVDAA    60
         |||||:::|||:|||||||||||  |||:||:||:|||||||||||||||:||||||
lamBor       MKKMLLATALALLITGCAQQTFTVQNKPAAVAPKETITHHFFVSGIGQKKTVDAA    55

Iss_Ec   KFVGGAENVVKTETQQTFVNALPGFITFGIYTPRETRVYCSQ    102
         |: |||||||||||||||||:| |||||||||| |:||||||
102Iss   KICGGAENVVKTETQQTFVNGLLGFITFGIYTPLEARVYCSQ    102
         |||||||||||||||||||||||||||:||||||||||||||
lamBor   KICGGAENVVKTETQQTFVNGLLGFITLGIYTPLEARVYCSQ    97
```

FIGURE 3

```
L    E    V    L    F    Q    G    P    L    G    S    M    Q    D    N
CTG GAA GTT CTG TTC CAG GGG CCC CTG GGA TCC ATG CAG GAT AAT
PreScission Protease                    BamHI   iss fusion start K    M    K    K    M    L    F    S    A    A    L    A    M    L    I
AAG ATG AAA AAA ATG TTA TTT TCT GCC GCT CTG GCA ATG CTT ATT T    G    C    A    Q    Q    T    F    T    V    G    N    K    P    T
ACA GGA TGT GCT CAA CAA ACG TTT ACT GTT GGA AAC AAA CCG ACA A    V    T    P    K    E    T    I    T    H    H    F    F    V    S
GCA GTA ACA CCA AAG GAA ACC ATC ACT CAT CAT TTC TTC GTT TCG G    I    G    Q    E    K    T    V    D    A    A    K    I    C    G
GGA ATT GGA CAA GAG AAA ACT GTT GAT GCA GCC AAA ATT TGT GGC G    A    E    N    V    V    K    T    E    T    Q    Q    T    F    V
GGT GCA GAA AAT GTT GTT AAA ACA GAA ACT CAG CAA ACA TTC GTA N    G    L    L    G    F    I    T    F    G    I    Y    T    P    L
AAT GGA TTG CTC GGT TTT ATC ACT TTT GGC ATC TAT ACT CCG CTG E    A    R    V    Y    C    S    Q    *
GAA GCC CGG GTA TAT TGC TCA CAA TAG TTG CCC ATC GAT ATG GGG AGC TCA TCT GCG AAT TCC
              EcoRI
```

DNA ENCODING AN AVIAN E. COLI ISS

GOVERNMENT FUNDING

The present invention was made with government support under Grant No. 1P20RR11817-01, awarded by the NIH. The U.S. Government has certain rights in this invention.

BACKGROUND OF THE INVENTION

Pathogenic *Escherichia coli* ("*E. coli*") is the causative agent of a variety of diseases in humans and animals, and often have the ability to avoid, resist or inactivate a multicellular organisms chemical and cellular defenses for a significant period of time after the host has been exposed to the pathogen. *E. coli* infection of the avian respiratory tract causes respiratory tract lesions and septicemia.

*E. coli* infections are often secondary to infections of birds by infectious bronchitis virus, Newcastle disease virus and Mycoplasma spp (Gross, *Disease of Poultry*, 8th ed., 270–278 (1984)). Three components present on the cell surface of *E. coli* assist in promoting the survival of *E. coli* from serum and phagocytosis (Timmis et al., *Current Topics in Micro. and Immunol.*, 118:197–218 (1985)). These three components are the acidic polysaccharide capsules, O-antigen lipopolysaccharide ("O-antigens") and outer membrane proteins ("OMPs"). Some types of O-antigens have been shown to mediate resistance to complement and to increase bacterial virulence (Moll et al., *FEMS Lett.*, 6:273–276 (1979); Pluschke et al., *Infect. Immun.*, 42:907–913 (1983); and Goldman et al., *J. Bacteriol.*, 159:877–882 (1984)). Avian *E. coli* strains with one of three O-antigens, O1, O2 or O3, cause the majority of all *E. coli*-induced septicemic colibacillosis in birds (Naveh et al., *Avian Disease*, 28:651–661 (1984)). However, many other serotypes such as O78:K80 are also observed.

Septicemic colibacillosis occurs most commonly in 5 to 12-week old broiler chickens, but also occurs in newly hatched chicks and turkey poults. The pathogenicity of *E. coli* for poultry has been correlated with various factors (Sussman, *The Virulence of Escherichia coli*, Academic Press Inc., Ltd., London (1985)). These factors include antimicrobial resistance (Cloud et al., *Avian Dis.*, 29:1084–1093 (1985)); production of colicins, siderophores, type I pili and hemolysins (Arp et al., *Avian Dis.*, 24:153–161 (1980)); resistance to host complement (Ike et al., *J. Vet. Med. Sci.*, 54:1091–1098 (1992)); presence of certain plasmids (Binns et al., *Nature*, 279:778–781 (1979)); motility (Wooley et al., *Avian Dis.*, 6:679–684 (1992)); serotype, e.g., O1, O2, O3 and O78 (Rosenberger et al., *Avian Dis.*, 29:1094–1107 (1985)); and invasiveness (Vidotto et al., *Avian Dis.*, 34:531–538 (1990)). Recent reports have shown that the ability of avian *E. coli* to resist the lytic effects of host complement is a major factor in the development of colibacillosis in poultry (Nolan et al., *Avian Dis.*, 38:146–150 (1994); Nolan et al., *Avian Dis.*, 3:395–397 (1992); Nolan et al., *Avian Dis.*, 36:398–402 (1992)).

Two well-defined, interacting components that constitute the major first-line of host defenses against invading bacteria are the complement system and phagocytosis (Miims, C. A., *The Pathogenesis of Infectious Disease*, 2nd edn. Academic, London (1982); Taylor, P. W., *Microbiol. Rev.*, 47:46–83 (1983)). Phagocytosis involves the ingestion of particulate material, including whole pathogenic microorganisms. In phagocytosis, the plasma membrane expands around the particulate material to form phagosomes. Only specialized cells, phagocytes, are involved in phagocytosis and include such cells as blood monocytes, neutrophils and tissue macrophages.

Complement resistance of *E. coli* has generally been reported as related to several potential structural factors including a K1-antigenic capsule (Aquero et al., *Infect. Immun.*, 40:359–368 (1984)), or other capsule type (Russo et al., *Infect. Immun*, 61:3578–3582 (1993)), a smooth lipopolysaccharide (LPS) layer (Cross et al., In: *Bacteria, Complement and the Phagocytic Cell*, Vol. H24, F. C. Cabello and C. Pruzzo, eds., Springer-Verlag, Berlin, pp. 319–334 (1988)), and certain OMPs including TraT (Montenegro et al., *J. Gen. Microbiol.* 131:1511–1521 (1985); Moll et al., *Infect. Immun.* 28:359–367 (1980)), Iss (Binns et al., *Infect. Immun.* 35:654–659 (1982); Chuba et al., *Mol. Gen. Genet.*, 216:287–192 (1989)), and OmpA (Weiser et al., *Infect. Immun.* 52:2252–2258 (1991)). The absence of capsule as a complement-resistance mechanism in disease-associated avian *E. coli* isolates suggests that such isolates must employ other means to avoid the killing effects of complement.

Iss is an OMP encoded by an avian *E. coli* iss gene. Some reports have indicated that *E. coli* isolates from avian subjects with a septicemic disease are much more likely to have iss-related sequences than are *E. coli* isolates of apparently healthy birds. However, no significant difference in the distribution of traT-related sequences (traT encodes the OMP TraT) has been found in the same isolates. The plasmid location of iss and traT suggests that their presence in different isolates might be more variable than the chromosomally-located ompA gene (Weiser et al., *Infect. Immun.*, 59:2252–2258 (1991)).

The expression of a human *E. coli* iss gene was found to increase the virulence of *E. coli* containing the gene by 100-fold for one-day old chicks and to increase the complement resistance of transformed cells over 20-fold for one-day old chicks (Binns et al., *Infect. Immun.*, 35:654–659 (1982)). Genetic evidence suggests that iss obtained from human *E. coli* is a derivative of a lambda gene known as bor (Barondess et al., *J. Bacteriol.*, 177:1247–1253 (1995); Barondess et al., *Nature*, 346:871–874; (1990); Chuba et al., *Mol. Gen. Genet.*, 216:287–292 (1989)). Bor is a lipoprotein of the cell envelope of *E. coli* lambda lysogens and appears to confer serum resistance on these lysogens. (Barondess et al., *J. Bacteriol.*, 177:1247–1253 (1995)). The high sequence identity between the Bor polypeptide and an avian Iss polypeptide suggests that Iss is also targeted to the outer membrane.

Septicemic colibacillosis is an economically devastating problem for the poultry industry in the United States. It is the most costly bacterial disease of production poultry animals causing multi-million dollar losses by the poultry industry annually. Control of this disease is hampered by the lack of a basic understanding about the virulence mechanisms employed by avian *E. coli*. For example, no single identifiable virulence marker has been associated with disease-causing avian *E. coli*. In other animal species, such as cattle, certain markers of virulence have been identified, and these markers have been used to facilitate epidemiologic studies and to develop control strategies designed to decrease the detrimental impact of colibacillosis on animal agriculture (Butler et al., *G. L. Gyles ed. CAB International*, Wallingford, UK:91–116 (1994)).

Therefore, a need exists to identify genes and other markers associated with complement-resistance of *E. coli* in birds. These genes can finction as markers for disease-causing avian *E. coli* and the detection of these genes may form the basis for improved diagnostic and control strategies for avian colibacillosis, in addition to the formulation and preparation of immunogenic compositions useful to prevent or inhibit avian septicemic diseases.

SUMMARY OF THE INVENTION iss has been identified as a marker for avian *E. coli* virulence and complement-resistance, and is associated with septicemic disease in birds. As used herein, the term iss or iss "gene" refers to a nucleic acid sequence or molecule that encodes an avian *E. coli* Iss polypeptide. Thus, the present invention provides an isolated and purified nucleic acid molecule that encodes an avian *E. coli* Iss polypeptide, a biologically active variant or subunit thereof. However, as described more fully below, an "Iss polypeptide" also includes an Iss "fusion" polypeptide.

A biologically active Iss polypeptide, variant or subunit thereof filing within the scope of the invention has at least about 1%, preferably at least about 10%, more preferably at least about 50%, and even more preferably at least about 90%, the activity of the polypeptide comprising SEQ ID NO:2. A preferred nucleic acid sequence is a DNA molecule encoding an Iss polypeptide (SEQ ID NO:2).

Another preferred embodiment of the invention is an isolated nucleic acid molecule comprising a nucleotide sequence as shown in FIG. 1 (SEQ ID NO:22). Biological samples from an avian subject suspected of being exposed to, a carrier of, or afflicted with a septicemic disease, such as colibacillosis, can be analyzed for the presence of an iss nucleic acid sequence or an Iss polypeptide sequence encoded thereby. The term "septicemia" or "septicemic disease" includes, but is not limited to, several avian diseases such as air-sacculitis, pneumonitis, septicemic colibacillosis and colisepticemia.

The present invention further provides an expression cassette comprising a preselected iss nucleic acid sequence operably linked to a promoter and functional in a host cell wherein said nucleic acid sequence encodes an Iss polypeptide, a biologically active variant or subunit thereof. The expression cassettes can be placed into expression vectors. These recombinant vectors can then be employed to transform prokaryotic and eukaryotic host cells. The expression of the preselected nucleic acid sequence in the transformed cell results in the production of recombinant Iss polypeptide or an Iss fuision polypeptide depending on the selected vector. As used herein, an Iss "fusion" polypeptide or protein is a product of a first preselected nucleic acid sequence, for example a preselected iss sequence, and a second nucleic acid sequence, for example a glutathione S-transferase sequence, operably linked at either the carboxyl terminal or amino terminal of the first sequence. The expression of this chimeric gene results in a single or continuous polypeptide or protein when expressed and isolated from a host cell. The product of this expression can enhance properties relating to, for example, purification, isolation, targeting and increased immunogenicity.

The present invention further provides a method for detecting a nucleic acid sequence encoding an avian *E. coli* Iss polypeptide comprising (a) contacting an amount of an avian *E. coli* DNA from a biological sample from a bird at risk of, or afflicted with, a septicemic disease, with an amount of at least two oligonucleofides under conditions effective to amplify the DNA so as to yield an amount of an amplified DNA sequence, wherein at least one oligonucleotide is specific for the nucleic acid of an avian *E. coli* iss nucleic acid sequence; and (b) detecting or determining the presence of the amplified DNA, wherein the presence of the amplified DNA is indicative of a bird at risk of, or afflicted with, a septicemic disease.

In yet another embodiment, a method of detecting nucleic acid molecules encoding an avian *E. coli* iss gene in a biological sample is provided comprising the steps of (a) introducing an avian *E. coli* iss specific oligonucleotide sequence and an iss non-specific oligonucleotide sequence into a biological sample suspected of containing an avian *E. coli* iss gene under conditions that permit the oligonucleotide sequences to hybridize to the avian *E. coli* iss gene, and (b) amplifying the hybridized sequences by polymerase chain reaction to yield an amplification product.

Techniques of nucleic acid detection include DNA and RNA amplification methods and includes such methods as polymerase chain reaction ("PCR"). Additionally, the detection of antibody responses specific for an Iss polypeptide encoded by an iss sequence can be used, for example, in ELISA-based immunoassays for the serodiagnosis of an avian subject suspected of being exposed to, a carrier of, or afflicted with a septicemic disease. The presence or amount of an iss or an Iss sequence in a sample can then be compared to a control sample, e.g., an avian subject known to be disease free.

Nucleic acid sequences of the invention can be produced by nucleic acid amplification techniques using novel oligonucleotide primers, such as, SEQ ID NOS:3, 4, 11, 12, 13, 14 and 15 employed in the synthesis. These novel primers can also used as probes and in PCR to detect other homologous iss nucleic acid sequences. An oligonucleotide or primer of the invention preferably has at least about 70%, more preferably at least about 85%, and most preferably at least about 90%, sequence identity or homology to SEQ ID NO:1.

The present invention also provides a polypeptide that can be used as a capture antigen to bind anti-polypeptide or anti-Iss antibodies in a biological sample obtained from an avian subject. For example, a biological sample comprising antibodies can be mixed with a purified Iss polypeptide to yield an antigen-antibody complex. The antibodies that are bound to the antigen are separated from the antibodies that are not bound to the antigen. The antigen-antibody complex is then detected or determined.

The invention further provides a method for detecting or determining the presence of Iss antibodies in a biological sample obtained from an avian subject. The method comprises contacting an amount of a purified Iss polypeptide, variant or subunit thereof with the biological sample that is suspected of comprising antibodies specific for the polypeptide for a sufficient time to form complexes between at least a portion of the antibodies and a portion of the purified polypeptide. The presence or amount of the complexes is then determined or detected.

In another embodiment of the present invention, monoclonal and polyclonal antibodies directed against an avian *E. coli* Iss polypeptide or fuision polypeptide are prepared. The recombinant polypeptide and antibodies are useful in the development of assays to detect Iss-producing *E. coli.*

In yet another embodiment of the invention, an avian Iss polypeptide, variant or subunit thereof can be used to produce populations of antibodies that, in turn can be used as the basis for assays to detect and quantify Iss polypeptide (or "protein") in samples derived from an avian subject. Also provided are populations of monoclonal and polyclonal antibodies that specifically bind to an avian *E. coli* Iss polypeptide or GST-Iss fusion protein. These antibodies can also be used in affinity chromatography, to purify avian Iss from natural sources.

Also provided is a diagnostic kit for detecting or determining antibodies that specifically react to an avian *E. coli* Iss polypeptide, variant or subunit thereof. The kit comprises packaging, containing, separately packaged, a solid phase capable of binding a polypeptide and a known amount of a purified Iss polypeptide. Preferably, the polypeptide has an amino acid sequence comprising SEQ ID NO:2, a biologically active variant or biologically active subunit thereof.

In another embodiment, an isolated and purified avian *E. coli* Iss polypeptide can be employed as a component in a diagnostic assay for "native" Iss in samples derived from avian biological samples. For example, polypeptide can be bound to a detectable label and employed in a competitive immunoassay for Iss protein.

Another preferred embodiment of the invention provides an immunogenic composition or a vaccine comprising an isolated and purified avian *E. coli* Iss polypeptide wherein the administration of the immunogenic composition or vaccine to an avian subject induces the production of antibodies to said polypeptide. The produced antibodies can inhibit or block subsequent infection of the host by a complement resistant and/or virulent avian *E. coli*. Preferably, the immunogenic composition or a vaccine is administered in combination with a pharmaceutically acceptable carrier.

BRIEF DESCRIPTION OF THE FIGURES

FIG. 1 shows partial alignment of the DNA sequence of the iss gene obtained from a virulent, complement-resistant avian *E. coli* isolate (102iss; SEQ ID NO:22), the DNA sequence of an iss gene from a septicemic human *E. coli* isolate (Eciss; SEQ ID NO. 5), and the DNA sequence of the lambda bor gene (lambor; SEQ ID NO.6).

FIG. 2 shows alignment of the predicted amino acid sequence of Iss from a virulent, complement-resistant avian *E. coil* (102 Iss; SEQ ID NO.2); Iss from a septicemic human *E. coli* isolate (Iss_Ec; SEQ ID NO.7), and the lambda Bor protein (lamBor; SEQ ID NO.8).

FIG. 3 shows the iss gene sequence (SEQ ID NO:22) cloned in frame into expression vector pGEX-6P-3 including the PRESCISSION protease cleavage site (SEQ ID NO:21). The polypeptide encoded by SEQ ID NO:21, designated SEQ ID NO:20, is also shown. The GST fuision sequence, not shown, is located upstream of the PRESCISSION protease cleavage site. The amplified iss gene was cloned into the BamHI and the EcoRI sites of the pGEX-6P-3 vector.

DETAILED DESCRIPTION OF THE INVENTION

Figure 4:
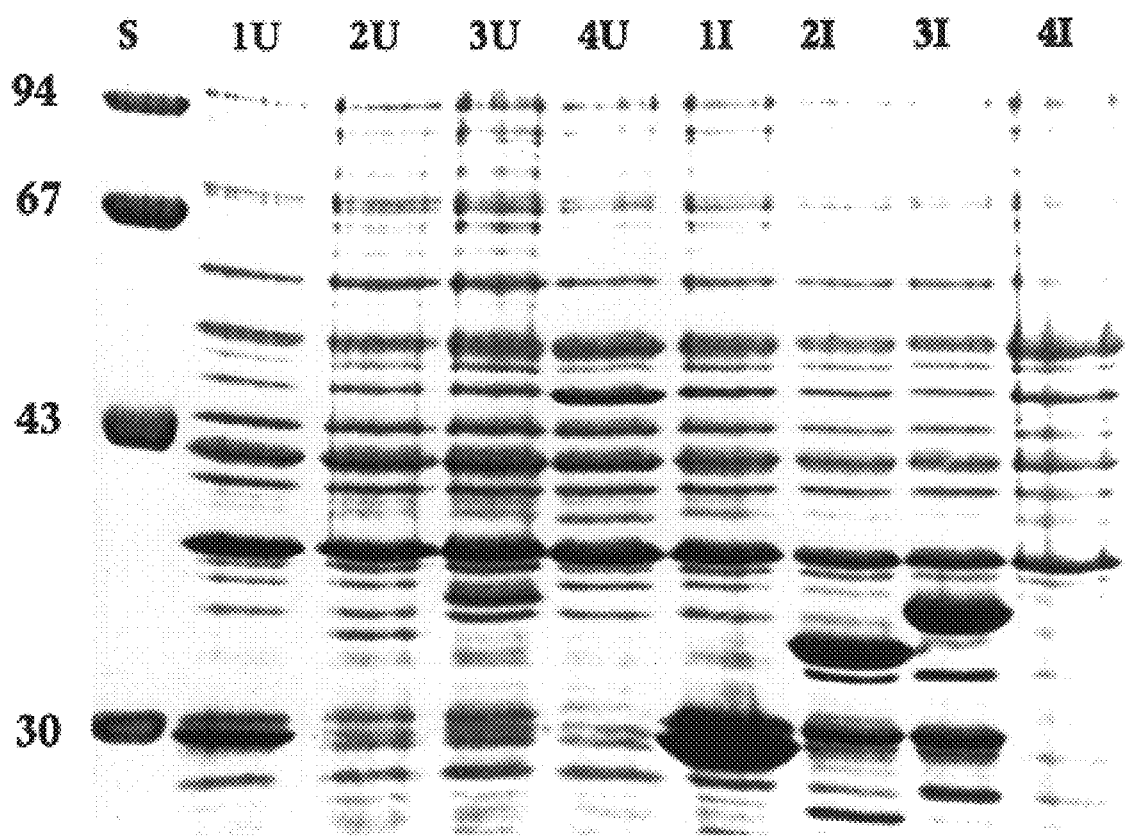
FIG. 4 shows an SDS-PAGE of crude total protein preparations of a protease-deficient *E. coli* containing the expression vector, pGEX-6P-3, or pGEX-6P-3 comprising the iss gene sequence, in the "uninduced" or "induced" state. Lane S=molecular weight standard in kD (Pharmacia Biotech Inc., Piscataway, N.J.); Lane 1U=pGEX-6P-3 alone in the "uninduced" state; Lane 3U=pGEX-6P-3 comprising iss in the "uninduced" state; Lane 1I=pGEX-6P-3 alone in the "induced" state; and lane 3I=pGEX-6P-3 comprising iss in the "induced" state. Note that lane 3I shows a 37 kD protein band not present in lanes 1U, 3U or 1I which is consistent with an GST-Iss fuision polypeptide product.

The identification and association of iss and Iss with clinical disease, e.g., septicemia, in birds due to virulent and complement resistant *E. coli* has been established. The data obtained from the isolation and characterization of iss and Iss sequences has clarified the disease-causing potential of isolates that carry the iss gene, and established the importance of Iss to avian *E. coli* virulence and complement resistance. Moreover, iss and Iss employed as markers enable the development of diagnostic procedures for use in avian colibacillosis outbreaks and epidemiological studies and provide development of such diagnostic procedures by production of, for example, monoclonal antibodies to Iss.

Definitions

In describing the present invention, the following terminology will be used in accordance with the definitions set out below.

The terms "isolated and/or purified," refer to in vitro preparation, isolation and/or purification of a nucleic acid molecule, polypeptide or peptide of the invention, so that it is not associated with in vivo substances.

As used herein, an "Iss polypeptide or amino acid sequence" is preferably an avian *E. coli* iss derived polypeptide having an amino acid sequence comprising SEQ ID NO:2, or a biologically active variant or subunit thereof. A "variant" Iss polypeptide is a polypeptide having an amino acid sequence that has at least about 87%, preferably at least about 90%, and more preferably at least about 95%, but less that 100%, sequence identity or homology to SEQ ID NO:2 or a biologically active subunit thereof. A variant polypeptide, peptide or amino acid sequence of the invention may include amino acid residues not present in the corresponding wild type Iss polypeptide or peptide, as well as internal deletions relative to the corresponding wild type Iss polypeptide. As used herein, a "subunit" is a biologically active portion, region or peptide of a full-length Iss polypeptide, e.g., SEQ ID NO:2.

Preferably, the polypeptides and peptides of the instant invention are biologically active. For example, biologically active Iss polypeptides, peptides and variants thereof falling within the scope of the invention have at least about 1%, preferably at least about 10%, more preferably at least about 50%, and even more preferably at least about 90%, the activity of the polypeptide comprising SEQ ID NO:2. The activity of an Iss polypeptide or peptide, can be measured by methods well known to the art including, but not limited to, the ability of the polypeptide, peptide to be bound by antibodies specific for Iss (e.g., specific for the Iss protein) or the ability of the polypeptide or peptide to elicit a sequence-specific immunologic response when the polypeptide is administered to an animal such as an avian subject. An avian *E. coli* Iss polypeptide, peptide, variant, subunit or fragment thereof is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

Preferably, the immunologic response is a humoral response, i.e, antibody response, directed to a particular epitope on the polypeptide or peptide. More preferably, the presence of antibodies specific for an Iss epitope correlates with a septicemic infection in an avian subject. As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8–10 such amino acids. Methods of determining the spatial conformation of amino acids are known in the art, and include, for example, x-ray crystallography and 2-dimensional nuclear magnetic resonance.

An isolated "variant" nucleic acid sequence of the present invention is a nucleic acid sequence that has at least 87%, preferably at least about 90%, and most preferably at least about 95%, but less than 100%, nucleic acid sequence identity or homology to a the nucleotide sequence of the corresponding wild type nucleic acid molecule, e.g., a DNA sequence comprising SEQ ID NO:22. However, a variant nucleic acid molecule of the invention may include nucleotide bases not present in the corresponding wild type nucleic acid molecule, as well as internal deletions relative to the corresponding wild type nucleic acid molecule. As used herein a nucleic acid "subunit" is a biologically active portion or region of a full-length iss nucleic acid sequence, e.g., SEQ ID NO:22.

The term "hybridization under stringent conditions" refers to those conditions that (1) employ low ionic strength and high temperature for washing, for example, 0.015 M NaCl/0.0015 M sodium citrate (SSC); 0.1% sodium lauryl sulfate at about 68° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM Nacl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

As used herein, the term "target region" refers to a region of the nucleic acid which is to be amplified and/or detected.

A "genomic clone" refers to a DNA fragment derived directly from cellular DNA rather than from messenger RNA, the usual source for cDNA clones. Genomic and cDNA clones have different sequences due to RNA splicing.

BACKGROUND

The general techniques used in cloning avian *E. coli* iss nucleic acid sequences (e.g., PCR technology, sequencing nucleic acid clones and polypeptides derived therefrom, constructing expression vectors or expression cassettes, transforming cells, performing immunological assays such as radioimmunoassays and ELISA assays, and growing cells in culture) are known in the art and laboratory manuals are available describing these techniques. See, for example, Sambrook, Fitsch & Maniatis, *Molecular Cloning*; A Laboratory Manual, Cold Spring Harbor Laboratory Press (1989); DNA Cloning, Volumes I and II (D. N. Glover ed. 1985); Oligonucleotide Synthesis (M. J. Gait ed, 1984); Nucleic Acid Hybridization (B. D. Hames & S. J. Higgins eds. 1984); Animal Cell Culture (R. I. Freshney ed. 1986); Immobilized Cells and Enzymes (IRL Press, 1986); B. Perbal; A Practical Guide to Molecular Cloning (1984); the Series, Methods in Enzymology (Academic Press, Inc.); Immunochemical Methods in Cell and Molecular Biology (Academic Press, London), Scopes, (1987), Protein Purification: Principles and Practice, Second Edition (Springer-Verlag, N.Y.), and Handbook of Experimental Immunology, Volumes I–IV (D. M. Weir and C. C. Blackwell eds 1986).

I. Identification of Isolates Falling Within the Scope of the Invention

A. Sources of Avian *E. coli* Isolates

*E. coli* iss isolates have been collected from a variety of avian subjects (e.g., turkeys, chickens and ducks) clinically diagnosed with a septicemic disease or exposed to other avians having, afflicted with, or suspected of a septicemic disease. Biological samples have been obtained from sources such as tissues, organs, blood, serum, bone and yolk sacs. As used herein, the term "biological sample" refers to material derived from, obtained from, or collected from the aforementioned sources of an animal. Preferably, the biological sample is from an avian subject. Other sources of nucleic acid sequences encoding avian *E. coli* Iss polypeptides can be derived from any eukaryotic source, preferably an avian farm animal, known or believed to be naturally or experimentally infected by a virulent, septicemic causing avian *E. coli*.

A phenotypic comparison of 40 avian *E. coli* iss isolates from the intestines of normal chickens and 40 avian *E. coli* iss isolates from the organs of colisepticemic chickens was performed. The isolates from colisepticemic chickens were shown to be more likely to produce siderophores and type I pili, and exhibit greater complement resistance, than were the intestinal isolates from normal chickens. A closer examination of the 10 most complement-resistant colisepticemic iss isolates and the 10 most complement-sensitive intestinal iss isolates revealed that an iss isolate's ability to resist complement directly correlated with an isolates ability to kill chick embryos (Wooley et al., *Avian Dis.*, 36:679–684 (1992)).

The lytic activity of complement on test isolates was determined by a quantitative microtiter test method (Lee et al., *Avian Dis.* 35:892–896 (1991)). The quantitative microtiter test results were analyzed by calculating the regression coefficients ($\beta$) of the slopes of growth over time. The $\beta$ values were ranked and compared using a Dunnett's test ($\alpha$=0.05). These rankings permitted the classification an *E. coli* as either sensitive, intermediate or resistant to the action of chicken complement. This observation was confirmed by mutational analysis. Specifically, a mutant *E. coli* differing from a virulent wild-type *E. coli* in the single factor of complement resistance was prepared and tested (Nolan et al., *Avian Dis.*, 36:398–402 (1992)). Characterization of this complement-sensitive mutant revealed that it was less virulent than the wild-type isolate (Kottom et al., *Avian Dis.* (1997); Nolan et al., *Avian Dis.*, 38:146–150 (1994); Nolan et al., *Avian Dis.*, 36:398–402 (1992)). This attribute provides further evidence that complement resistance is an important contributor in the observed virulence of avian *E. coli*.

The occurrence of iss related sequences among clinical human and avian *E. coli* isolates is very informative. For example, Femendez-Beros et al., *J. Clin. Micro.*, 28:742–746 (1990) examined 200 *E. coli* isolates from patients with diarrhea and 146 isolates from patients with bacteremia for their possession of several virulence-related sequences including traT and iss. No difference was found between the two groups in distribution of these two genes. The iss-related sequences occurred in about 25–28% of all isolates examined, and the traT-related sequences occurred in 41–44% of these same isolates.

In the present invention, 210 isolates, derived from a variety of sources, such as tissue, bone, blood, serum and yolk sacs of birds with colibacillosis and 56 fecal isolates of healthy birds were examined. It was found that 76% of the isolates of sick chickens contained iss-related sequences, and only 23% of the isolates of healthy chickens contained such sequences. There was no significant difference in the distribution of traT-related sequences between the two groups, suggesting that traT was not an important virulence factor for avian *E. coli* isolates. Conversely, the large difference in the distribution of iss among isolates of birds suggests iss was a potentially important virulence factor for avian *E. coli*. Additionally, the difference in distribution of iss-related sequences in isolates from birds and humans with extraintestinal colibacillosis suggested that iss was potentially more important for complement resistance and virulence with avian *E. coli* than with human *E. coli*.

The differences in the distribution of iss and capsule, a polysaccharide layer located outside the cell wall of bacteria, among avian and human *E. coli* isolates further emphasize the intriguing differences between avian and mammalian colibacillosis and suggest that the avian model of colibacillosis is a unique system in which to observe complement resistance. The uniqueness of this system reflects the nature of colibacillosis in birds, the entry point of *E. coli* into a host bird, and the initial sites of colonization of the host. As mentioned previously, the route of entry for most forms of avian colibacillosis is the respiratory tract. Enteric forms of avian colibacillosis are rare (Gyles, In: *Pathogenesis of Bacterial Infections in Animals*, 2nd ed., C. L. Gyles and C. O. Thoen, eds., Iowa State University Press, Ames, IA, pp. 164–187 (1993)). This is not the case in mammals, where intestinal forms of colibacillosis are common (Gyles, In: *Pathogenesis of Bacterial Infections in Animals*, 2nd ed., C. L. Gyles and C. O. Thoen, eds., Iowa State University Press, Ames, IA, pp. 164–187 (1993)). Moreover, the entry point taken by most disease-causing *E. coli* of avians is primarily through the respiratory tract, unlike mammals, wherein the route of initial entry is likely to be the gastrointestinal tract (Gyles, In: *Pathogenesis of Bacterial Infections in Animals*, 2nd ed., C. L. Gyles and C. O. Thoen, eds., Iowa State University Press, Ames, IA, pp. 164–187 (1993)).

B. Isolation of Nucleic Acid Molecules of the Invention

A nucleic acid molecule encoding an Iss polypeptide can be identified and isolated using standard methods, as described by Sambrook et al., (1989). For example, polymerase chain reaction can be employed to isolate and clone iss genes. "Polymerase chain reaction" or "PCR" refers to a procedure or technique wherein amounts of a preselected piece of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite or complimentary strands of the template to be amplified. PCR can be used to amplify specific RNA sequences, specific DNA sequences from total genomic DNA, and cDNA transcribed from total cellular RNA, bacteriophage or plasmid sequences and the like, to yield an amplification product. See also, Mullis et al., *Cold Harbor Symp. Ouant. Biol.*, 51:263 (1987); Erlich, ed., *PCR Technology* (Stockton Press, NY, 1989).

iss nucleic acid sequences can be isolated from septicemic bird tissue samples by PCR techniques employing iss specific oligonucleotide primers, for example, SEQ ID NO.3,4, 11, 12, 13, 14, and 15. These primers will be identical or similar in sequence to opposite strands of the template to be amplified. Primers are made to correspond to nucleic acid molecules encoding highly conserved regions of polypeptides. However, these nucleic acid molecules can be introduced into expression cassettes, which, when expressed in a host, can provide "anti-sense" nucleic acid transcripts. Thus, the present invention also provides isolated and purified "antisense" nucleic acid molecules that have at least about 80%, preferably about 90%, and most preferably at least about 98%, nucleotide sequence complementary to SEQ ID NOs.1, 11, 12, 13, 14 and 15.

Alternatively, nucleotide sequences can be obtained and prepared by a sequence comparison of other related genes, such as the traT and ompA sequences. Preferably, at least two primers are prepared, one of which is predicted to anneal to the antisense strand, and the other of which is predicted to anneal to the sense strand of a nucleic acid molecule that encodes the avian *E. coli* Iss polypeptide. The products of each PCR reaction are separated by agarose gel electrophoresis, and the consistently amplified products are purified and cloned directly into a suitable vector such as a plasmid vector. Products obtained therefrom can be sequenced manually using standard procedures or with an automated sequencer, for example, LICOR™.

Alternatively, DNA libraries may be probed using the procedure of Grunstein and Hogness *Proc. Natl. Acad. Sci. USA*, 7:3961 (1975), or other available techniques as described in Sambrook et al. Briefly, in this procedure, the DNA to be probed is immobilized on a membrane (e.g., nitrocellulose or nylon filters) denatured, and prehybridized with a buffer containing 0–50% formamide, 0.75 M NaCl, 75 mM Na citrate, 0.02% (wt/v) each of bovine serum albumin, polyvinyl pyrollidone, and Ficoll, 50 mM Na Phosphate (pH 6.5), 0.1% SDS, and 100 micrograms/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and/or longer hybridization times. Both non-radioactive and radioactive techniques can be utilized. Probes containing more than 30 or 40 nucleotides such as those derived from genomic sequences generally employ higher temperatures, e.g., about 40°–42° C., and a high percentage, e.g., 50%, formamide. Following prehybridization, 5'-$^{32}$P-labeled oligonucleotide probe is added to the buffer, and the filters are incubated in this mixture under hybridization conditions. After washing, the treated filters are subjected to autoradiography or a non-radioactive technique such as DIGOXIGENIN™ D/UTP labeling kit (Boehringer Mannheim, Indianapolis, Ind.), to show the location of the hybridized probe; DNA in corresponding locations on the original agar plates is used as the source of the desired DNA.

The nucleotide sequence of an avian *E. coli* iss gene has about a 96.8% sequence identity in a 310 bp overlap, as shown in FIG. 1, when compared to the entire sequence of a human *E. coli* iss gene (Chuba et al., *Mol. Gen. Genet.*, 216:287–292 (1989)). Surprisingly, the avian *E. coli* iss gene has an insertion at nucleotide 158 and a deletion at nucleotide 189, that results in a frameshift in the resulting polypeptide sequence (SEQ ID NO.2). The 10 amino acid change located in the middle of the protein creates an approximate 86.3% sequence identity in a 102 amino acid overlap, as shown in FIG. 2, between the human ("Iss_Ec") and avian ("102 Iss") *E. coli* Iss polypeptides. The 102 Iss amino acid sequence and the Iss_Ec amino acid sequence are about 86.3% identical in a 102 amino acid overlap. The low identity between these two E. coli Iss sequences is due to a frameshift that has occurred in (Iss_Ec). The amino-terminal region of 102 Iss has structural features characteristic of a cleavable signal sequence and spans amino acids 17 to 22. Residues 17–21 of Iss are almost identical to residues 12–17 of Bor (FIG. 2).

When the avian E. coli iss sequence was examined with Gene Inspector™ software (Textco, Inc., West Lebanon, N.H.), it was found that the avian E. coli Iss protein is predicted to have an isoelectric point of approximately 8.47, and at pH 7, is expected to have a net charge of +2.05. An Iss polypeptide is predicted to be approximately a 10–11 kD protein containing 102 amino acids that is resistant to acid hydrolysis. Additionally, based on the Iss polypeptide's predicted folding characteristics and hydropathy plots, Iss is likely to have a number of accessible sites, for example, sites not buried in the bacterial membrane, that are antigenic.

The iss locus of the conjugative plasmid ColV, I-K94, is closely related to the phage lambda bor gene. Sequencing has shown that iss displays a discrete 796 bp block of DNA homologous to a region from bp 46186 to 46982 in the lambda sequence (Chuba et al., *Mol. Gen. Genet.*, 216:287–292 (1989); Sanger et al., *J, Mol. Biol.*, 162:729–773 (1982)). The overall identity between lambda bor and iss is about 81%, excluding gaps, as the avian E. coli iss nucleotide sequence has an approximate 89.4% sequence identity in a 303 bp overlap with the lambda bor gene (Barondess et al., *J. Bacteriol.*, 177:1247–1253 (1995); Barondess et al., *Nature*, 346:871–874 (1990)). The 102 Iss amino acid sequence and the lamBor amino acid sequence are about 89.7% identical in a 97 amino acid overlap.

C. Variants of the Nucleic Acid Molecules of the Invention

Nucleic acid molecules encoding amino acid sequence variants of an Iss polypeptide can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an Iss polypeptide.

Oligonucleotide-mediated mutagenesis is a preferred method for preparing amino acid substitution variants of an Iss polypeptide. This technique is well known in the art as described by Adelman et al., *DNA* 2:183 (1983), and Zoller *Nucleic Acids Res.*, 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified and having the desired modification included in its own sequence. The resulting double-stranded DNA is transformed into a phage supporting host bacterium. As used herein, a "double-stranded DNA molecule" refers to the polymeric form of deoxyribonucleotides (adenine, guanine, thymine or cytosine) in its normal, double-stranded helix. This term refers only to the primary and secondary structure of the molecule, and does not limit it to any particular tertiary forms. Thus this term includes double-stranded DNA found, inter alia, in linear DNA molecules (e.g., restriction fragments), viruses, plasmids and chromosomes. In discussing the structure of a particular double-stranded DNA molecules, sequences may be described herein according to the normal convention of giving only the sequence in the 5' to 3' direction along the non-transcribed strand of DNA (i.e., the strand having a sequence homologous to the mRNA). Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to a labeled synthetic probe at temperatures and conditions that permit hybridization with the correct strand, but not with the unmodified sequence. The sequences which have been identified by hybridization are recovered and then cloned.

A DNA sequence encoding an Iss polypeptide can be synthetically prepared rather than isolated. The DNA sequence can be designed with the appropriate codons for an Iss amino acid sequence or variant thereof. In general, one will select preferred codons for the intended host if the sequence will be used for expression. The complete sequence is assembled from overlapping nucleotides prepared by standard methods and assembled into a complete coding sequence. See, e.g., Edge, *Nature*, 292:756 (1981); Nambair et al., *Science* 2:1299 (1984); Jay et al., *J. Biol. Chem.* 2:6311 (1984). Additionally, synthetic iss oligonucleotide sequences may be prepared using an automated oligonucleotide synthesizer as described by Warner *DNA*, 3:401 (1984).

Additionally, nucleotide substitutions in SEQ ID NO:22 that can encode a polypeptide having SEQ ID NO:2 or variant thereof can be ascertained by reference to Table 1 and page D1 in Appendix D of Sambrook et al., *Molecular Cloning: A Laboratory Manual* (1989), as well as Table 1 hereinbelow. Nucleotide substitutions can be introduced into DNA segments by methods well known to the art, some of which are described above. See, also, Sambrook et al., supra. Likewise, nucleic acid molecules encoding other Iss polypeptides may be modified in a similar manner. Thus, nucleic acid molecules encoding at least a portion of SEQ ID NO:2, or the complement thereto, may be modified so as to yield nucleic acid molecules of the invention having "silent" nucleotide substitutions, or to yield nucleic acid molecules having nucleotide substitutions that result in amino acid substitutions (see polypeptide or peptide variants hereinbelow).

TABLE 1

| Amino Acid | Codon |
| --- | --- |
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

D. Preparation of Expression Cassettes and Vectors and Their Introduction into Host Cells To prepare expression cassettes and vectors for transformation herein, the recombinant or preselected nucleic acid sequence or segment may be circular or linear, double-stranded or single-stranded. As used herein, a "vector," "expression vector," or "expression cassette" is a replicon, or a genetic element that functions as an autonomous unit of DNA replication in vivo and capable of replication under its own control, such as a plasmid, a chromosome, a virus, phage or cosmid. Another DNA segment may be attached to the replicon or genetic element so as to bring about the replication of the attached segment.

Expression cassettes or expression vectors for host cells ordinarily include an origin of replication, a promoter located upstream from the Iss coding sequence, together with a ribosome binding site, a polyadenylation site, and a transcriptional termination sequence. Those of ordinary skill will appreciate that some of the aforementioned sequences are not required for expression in certain hosts. For example, an expression vector for use with microbes need only contain an origin of replication recognized by the host, a promoter that will finction in the host and a selection gene.

An expression cassette is constructed according to the present invention so that an avian *E. coli* iss coding sequence is located in the cassette with the appropriate regulatory sequences, the positioning and orientation of the coding sequence with respect to the control sequences being such that the coding sequence is transcribed under the "control" of the control sequences (e.g., RNA polymerase that binds to the DNA molecule as the control sequences transcribes the coding sequence). As used herein, a DNA "coding sequence" is that portion of a DNA sequence, the transcript of which is translated into a polypeptide in vivo when placed under the control of appropriate regulatory sequences. The boundaries of the coding sequence are determined by a start codon at the 5' (amino terminus) and a translation stop codon at the 3' (carboxy terminus). A coding sequence can include, but is not limited to, prokaryotic sequences, genomic DNA sequences from eukaryotic DNA, cDNA from eukaryotic mRNA and even synthetic DNA sequences. A polyadenylation signal and transcription termination sequence will usually be located 3' to the coding sequence.

The control sequences can be ligated to the coding sequence prior to insertion into a cassette. As used herein, a coding sequence is "under the control" of the promoter sequence in a cell when RNA polymerase which binds the promoter sequence transcribes the coding sequence into mRNA which is then in turn translated into the protein encoded by the coding sequence. Alternatively, the coding sequence can be cloned directly into an expression cassette that already contains the control sequences and an appropriate restriction site.

1. Transformations

Transformation may be by any known method for introducing polynucleotides into a host cell, including, for example, packaging the polynucleotide in a virus and transducing a host cell with the virus, and by direct uptake of the polynucleotide. The terms "transformed" or "transformation" or "stably transformed", as used herein, refer to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome. A cell has been "transformed" by exogenous DNA when such exogenous DNA has been introduced into the cell membrane. Exogenous DNA may or may not be integrated (covalently linked) to chromosomal DNA making up the genome of the cell. In prokaryotes and yeast, for example, the exogenous DNA may be maintained on an episomal element such as a plasmid. With respect to eukaryotic cells, a stably transformed cell is one in which the exogenous DNA has become integrated into a chromosome so that it is inherited by daughter cells through chromosomal replication. This stability is demonstrated by the ability of the eukaryotic cell to establish cell lines or clones comprised of a population of daughter cells containing the exogenous DNA.

The transformation procedure used depends upon the host to be transformed. Bacterial transformation by direct uptake generally employs treatment with calcium or rubidium chloride (Cohen *Proc. Natl. Acad. Sci. USA*, 69:2110 (1972)). Yeast transformation by direct uptake may be carried out using the method of Hinnen et al. *Proc. Natl. Acad. Sci.*, 75:1929 (1978). Mammalian transformations by direct uptake may be conducted using the calcium phosphate precipitation method of Graham and Van der Eb *Virology*, 52:546 (1978), or the various known modifications thereof. Other methods for the introduction of recombinant polynucleotides into cells, particularly into mammalian cells, that are known in the art include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

As used herein, the term "recombinant nucleic acid," refers to a nucleic acid that has been derived or isolated from any appropriate source, that may be subsequently chemically altered in vitro, and later introduced into target host cells. An example of recombinant DNA "derived" from a source, would be a DNA sequence that is identified as a useful fragment encoding iss, or a fragment or a variant thereof, and which is then chemically synthesized in essentially pure form. An example of such DNA "isolated" from a source would be a useful DNA sequence that is excised or removed from said source by chemical means, for example, by the use of restriction endonucleases. The isolated sequence can then be further manipulated, such as, amplified for use in the invention, by the methodology of genetic engineering.

"Recombinant host cells," "host cells," "cells," "cell lines," cell cultures," and other such terms denoting microorganisms or higher eukaryotic cell lines cultured as unicellular entities refer to cells that can be, or have been used as recipients for a recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental or deliberate mutation.

2. Cellular hosts

Both prokaryotic and eukaryotic host cells may be used for expression of desired coding sequences. Appropriate control sequences that are compatible with the designated host should be used. The term "control sequences" is defined to mean DNA sequences necessary for the expression of an operably linked coding sequence in a particular host organism. The term "operably linked" is defined to mean that the nucleic acids are placed in a functional relationship with another nucleic acid sequence. For example, DNA for a presequence or secretory leader is operably linked to DNA for a polypeptide or fusion polypeptide if it is expressed as a pre-protein that participates in the secretion of the polypeptide or fusion polypeptide; a promoter or enhancer is "operably linked" to a coding sequence if it affects the transcription of the sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The control sequences that are suitable for prokaryotic cells, for example, include a promoter and optionally an operator sequence, and a ribosome binding site. A "promoter" or "promoter sequence" is a DNA regulatory region to which RNA polymerase binds and initiates transcription of a downstream (3' direction) coding sequence. For purposes of defining the present invention, the promoter sequence is bounded at its 3' terminus by the translation start codon of a coding sequence and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the -10 and -35 consensus sequences.

Eukaryotic cells are known to utilize promoters, polyadenylation signals and enhancers. Expression control sequences for prokaryotes include promoters, optionally containing operator portions and ribosome binding sites. Among prokaryotic hosts, *E. coli* is most frequently used. A number of prokaryotic expression vectors are known in the art. See, for example, U.S. Pat. Nos. 4,440,859; 4,436,815; 4,431,740; 4,431739; 4,428,941; 4,425,437; 4,418,149; 4,411,994; 4,366,246; 4,342,832; see also U.K. Pub. NOs. GB 2,121,054; GB 2,008,123; GB 2,007,675; and European Pub. No. 103,395.

Transfer vectors compatible with prokaryotic hosts are commonly derived from pBR322, a plasmid containing operons conferring ampicillin and tetracycline resistance, and various pUC vectors, which also contain sequences conferring antibiotic resistance markers. These markers may be used to obtain successful transformants by selection. Preferably, expression vectors obtained commercially from Pharmacia are utilized and include pGEX-1λT (product No. 27-4805-01), pGEX-2T (product No. 27-4801-01), pGEX-2TK (product No. 27-4587-01), pGEX-4T-1 (product No. 27-4580-01), pGEX-4T-2 (product No. 27-4581-01), pGEX-4(product No. 27-4583-01), pGEX-3X (product No. 27-4803-01), pGEX-5X-1 (product No. 27-4584-01), pGEX-5X-2 (product No. 27-4585-01), pGEX-5X-3 (product No. 27-4586-01), pGEX-6P-1 (product No. 27-4597-14 01), pGEX-6P-2 (product No. 27-4598-01) and pGEX-6P-3 (product No. 27–4599–01). Expression of iss in these vectors yields an GST-Iss fuision protein that can be employed to prepare antibodies, immunogenic compositions, vaccines and diagnostic kits. Alternatively, the Iss polypeptide can be cleaved from GST with PreScission™ protease (Pharmacia Biotech. Inc.) or other suitable enzyme, purified, and the Iss polypeptide can independently be employed to prepare antibodies, immunogenic compositions, vaccines and diagnostic kits.

Commonly used prokaryotic control sequences include the Beta-lactamase (penicillinase) and lactose promoter systems (Chang et al. *Nature*, 198: 1056 (1977)), the tryptophan (trp) promoter system (Goeddel et al. *Nucleic Acids Res.*, 8:4057 (1980)) and the lambda-derived PL promoter and N gene ribosome binding site (Shimatake et al. *Nature*, 292:128 (1981)) and the hybrid tac promoter (De Boer et al. *Proc. Natl. Acad. Sci. USA*, 292:128 (1983)) derived from sequences of the trp and lac UV5 promoters. The foregoing systems are particularly compatible with *E. coli*. If desired, other prokaryotic hosts such as strains of Bacillus or Pseudomonas may be used with appropriate control sequences. Although the promoters cited above are commonly used, other microbial promoters know in the art, are also suitable.

For routine vector constructions, ligation mixtures are transformed into *E. coli* strain HB101 or other suitable host, and successful transformants selected by antibiotic resistance or other markers. Plasmids from the transformants are then prepared according to the method of Clewell et al. *Proc. Natl. Acad. Sci. USA*, 62:1159 (1969), usually following chloramphenicol amplification (Clewell *J, Bacteriol.*, 110:667 (1972)). The DNA is isolated and analyzed, usually by restriction enzyme analysis and/or sequencing. Sequencing may be by the dideoxy method of Sanger et al. *Proc. Natl. Acad. Sci. USA*, 74:5463 (1977) as further described by Messing et al. *Nucleic Acids Res.*, 9:309 (1981), or by the method of Maxam et al. Methods in Enzymology, 65:499 (1980). Problems with band compression, which are sometimes observed in GC rich regions, are overcome by use of 7-deazoguanosine according to Barr et al. *Biotechniques*, 4:428 (1986).

Eukaryotic hosts include yeast and mammalian cells in culture systems. *Saccharomyces cervisiae* and *Saccharomyces carlsbergensis* are the most commonly used yeast hosts and are convenient fingal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach et al. *Meth. Enz.*, 101:307 (1983)), the combination of CEN3 and ARS1 or other means for assuring replication, such as sequences which will result in incorporation of an appropriate fragment into the host cell genome.

Control sequences for yeast vectors are known in the art and include promoters for the synthesis of glycolytic enzymes (Hess et al. *J. Adv. Enzyme Reg*, 7:149 (1968)); (Holland et al. *Biochemistry*, 17:4900 (1978)), including the promoter for 3 phosphoglycerate kinase (Hitzeman et al. *J. Biol. Chem.*, 255:2073 (1980)). Terminators may also be included, such as those derived from the enolase gene (Holland et al. *J. Biol Chem.*, 2:1385 (1981)). Particularly useful control systems are those that comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast alpha factor.

In addition, an operably linked transcriptional regulatory region and transcriptional initiation region do not have to be ones that are naturally associated in a wild-type organism. These systems are described in detail in EPO 120,551, granted Aug. 1, 1990; EPO 116,201, granted Apr. 22, 1992; and EPO 164,556, granted Mar. 2, 1992, and are hereby incorporated herein by reference. Other yeast promoters, which have the additional advantage of transcription controlled by growth conditions, are the promoter regions for alcohol dehydrogenase 1 or 2, isocytochrome C, acid phosphatase, as well as enzymes responsible for maltose and galactose utilization.

Mammalian cell lines available as hosts for expression are known in the art. Suitable host cells for expressing Iss in higher eukaryotes include the following: monkey kidney CVI line transformed by SV40 (COS-7, ATCC CRL 1651); baby hamster kidney cells (BHK, ATCC CRL 1651); Chinese hamster ovary-cells-DHFR (described by Urlaub and Chasin, *PNAS*, 77:4216 (1980, USA)); mouse sertoli cells (TM4. Mather, J. P., *Biol. Reprod.*, 23:243–251 (1980)); monkey kidney cells (CVI ATCC CCL 70): African green monkey kidney cells (VERO-76, ATCC CRL-1587): human cervical carcinoma cells (HELA, ATCC CCL 2); canine kidney cells (MDCK, ATCC CCL 34); buffalo rat liver cells (BRL 3A ATCC CRL 1442); human lung cells (W138, ATCC CCL 75): human liver cells (Hep G2 HB 8065); mouse mammary tumor (MMT 060652, ATCC CCL 51); rat hepatoma cells (HTC. M1.54. Baumann et al., *J. Cell Biol.*, 85:1–8 (1980) and TRI cells (Mather et al., *Annals N.Y. Acad. Sci.*, 3:44–68 (1982)).

Suitable promoters for mammalian cells are also known in the art and include viral promoters such as that from Simian Virus 40 (SV40) (Fiers et al. *Nature*, 273:113 (1978)), Rous sarcoma virus (RSV), adenovirus (ADV), and bovine papilloma virus (BPV). Mammalian cells may also require terminator sequences and poly A addition sequences; enhancer sequences that increase expression can also be included, and sequences which cause amplification of the gene may also be desirable. These sequences are known in the art. It will be appreciated that when expressed in mammalian tissue, a recombinant Iss may have higher molecular weight due to glycosylation. It is therefore intended that partially or completely glycosylated forms of Iss having molecular weights greater than provided by the amino acid back-bone are within the scope of this invention.

Vaccinia virus may be used to express foreign DNA and may be used in vaccine preparation. In this case the heterologous DNA is inserted into the Vaccinia genome. Techniques for the insertion of foreign DNA into the vaccinia virus genome are known in the art, and use, for example, homologous recombination. The insertion of the heterologous DNA is generally into a gene that is non-essential in nature, for example, the thymidine kinase gene (tk), which also provides a selectable marker. Plasmid vectors that greatly facilitate the construction of recombinant viruses have been described (see, for example, Mackett et al. *J. Virol*., 49:857 (1984), Chakrabarti et al. *Mol. Cell Biol.* 5:3403 (1985); Moss, *Gene Transfer Vectors for Mammalian Cells*, (Miller and Calos, eds., Cold Spring Harbor Laboratory, Cold Spring Harbor, N.Y.), p.10 (1987)). Expression of the Iss polypeptide then occurs in cells or animal subjects, e.g., avians, that are immunized with the live recombinant vaccinia virus.

Other systems for expression of eukaryotic or viral genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373. The vector pAc373 also contains the polyhedrin polyadenylation signal and the ampicillin-resistance (amp) gene and origin of replication for selection and propagation in *E. coli*. Many other vectors, known to those of skill in the art, have also been designed for improved expression. These include, for example, pVL985 (which alters the polyhedrin start codon from ATG to ATT, and which introduces a BamHI cloning site 32 base pairs downstream from the ATT; See Luckow and Summers Virology, 17:31 (1989)). Good expression of nonfused foreign proteins usually requires foreign genes that ideally have a short leader sequence containing suitable translation initiation signals preceding an ATG start signal.

Methods for the introduction of heterologous DNA into the desired site in the baculovirus virus are known in the art. (See Summer and Smith, Texas Agricultural Experiment Station Bulletin No. 1555; Smith et al. *Mol. & Cell Biol*., 3:2156–2165 (1983); and Luckow and Summers, supra (1989)). For example, the insertion can be into a gene such as the polyhedrin gene, by homologous recombination. Insertion can also be into a restriction enzyme site engineered into the desired baculovirus gene. The inserted sequences may be those which encode all or varying segments of the polyprotein, or other open reading frames ("ORFs") which encode viral polypeptides.

The signals for posttranslational modifications, such as signal peptide cleavage, proteolytic cleavage and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin 2 signal ($IL2_s$) which is a signal for transport out of the cell, is recognized and properly removed in insect cells.

In a preferred embodiment, the product upon expression of an avian *E. coli* Iss polypeptide yields an Iss-fusion protein that can be purified by affinity chromatography using a commercially available kit with an affinity for the fusion protein (Pharmacia, GST Gene Fusion System, Third Edition, Revision 1 (1997) (product No.18-1123-20), Bulk GST Purification Module (product No. 27-4570-01), Redipack GST Purification Module (product No. 27-4570-02). Once the Iss-fusion protein has been purified, Iss is cleaved from the fusion protein and utilized to immunize mice, e.g., Balb/c. However, an Iss fusion protein can be substituted as the immunogen if desired, although use of Iss alone is preferred. Spleen cells from the immunized mice showing a response to Iss or an Iss fusion protein are fused with myeloma cells to create hybridomas, and hybridomas producing antibody specific to Iss are propagated, characterized and retained for use in immunologic assays to define the association of Iss with avian *E. coli* virulence.

E. Polypeptides. Peptides and Variants Thereof

A recombinant or derived Iss polypeptide, as described above, is not necessarily translated from a designated nucleic acid sequence, for example, SEQ ID NO.22. Iss polypeptides, antigenic variants and subunits thereof, or other Iss subunit polypeptides can be synthesized by the solid phase peptide synthesis (or Merrifield) method or be prepared by a variety of methods known in the art. These and other methods of peptide synthesis are also exemplified by U.S. Pat. Nos. 3,862,925; 3,842,067; 3,972,859; 4,105,602 and 4,757,048.

The Merrifield method is an established and widely used method. It is described in the following references: Stewart et al., *Solid Phase Peptide Synthesis*, W. H. Freeman Co., San Francisco (1969); Merrifield, *J. Am. Chem. Soc*., 85:2149 (1963); Meinenhofer in Hormonal *Proteins and Peptides*, Vol. 2, C. H. Li, ed., (Academic Press, 1973), pp. 48–267; and Barany and Merrifield in "The Peptides," Vol. 2, E. Gross and F. Meinenhofer, eds., Academic Press (1980), pp. 3–285.

The Merrifield synthesis method commences from the carboxy-terminal end of the peptide using an alpha-amino protected amino acid. Fluorenylmethyloxy-carbonyl (Fmoc) or t-butyloxycarbonyl (Boc) protective groups can be used for all amino groups even though other protective groups are suitable, and the first protected amino acids can be esterified to chloromethylated polystyrene resin supports. The polystyrene resin support is preferably a copolymer of styrene with about 0.5 to 2% divinyl benzene as a cross-linking agent which causes the polystyrene polymer to be insoluble in certain organic solvents. See Carpino et al., *J. Org. Chem.*, 37:3404 (1972); Meinenhofer, *Int. J. Peat. Pro. Res.*, 11:246 (1978); and Merrifield, *J. Am. Chem. Soc.*, 85:2149 (1963). The immobilized peptide is then N-deprotected and other amino acids having protected amino groups are added in a stepwise manner to the immobilized peptide. At the end of the procedure, the final peptide is cleaved from the resin, and any remaining protecting groups are removed by treatment under acidic conditions, for example, with a mixture of hydrobromic acid and trifluoroacetic acid. Alternatively, the cleavage from the resin may be effected under basic conditions, for example, with triethylamine, where the protecting groups are then removed under acidic conditions. The cleaved peptide is isolated and purified by means well known in the art, for example, by lyophilization followed by either exclusion or partition chromatography on polysaccharide gel media such as Sephadex G-25, or countercurrent distribution. The composition of the final polypeptide may be confirmed by amino acid analysis after degradation of the polypeptide by standard means.

The synthesis may use manual techniques or be completely automated. For example, an Applied BioSystems 431A Peptide Synthesizer (Foster City, Calif.) or a Biosearch SAM II automatic peptide synthesizer (Biosearch, Inc., San Rafael, Calif.) can be employed following the directions provided in the instruction manual and reagents supplied by the manufacturer. Disulfide bonds between Cys residues can be introduced by mild oxidation of the linear peptide by KCN as taught in U.S. Pat. No. 4,757,048 at column 20.

Salts of carboxyl groups of a polypeptide, peptide or variant of the invention may be prepared in the usual manner by contacting the peptide with one or more equivalents of a desired base, for example, a metallic hydroxide base (e.g., sodium hydroxide), a metal carbonate or bicarbonate base, for example, sodium carbonate or sodium bicarbonate, or an amine base, for example, triethylamine or triethanolamine. Acid addition salts of the peptide may be prepared by contacting the peptide with one or more equivalents of the desired inorganic or organic acid, for example, hydrochloric acid.

Esters of carboxyl groups of the polypeptides may be prepared by any of the usual methods known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus, the C-terminal of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester. This cleavage is followed by aminolysis with the desired amine.

N-acyl derivatives of an amino group of a polypeptide, peptide or variant of the invention may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. Formyl-methionine, pyroglutamine and trimethyl-alanine may also be substituted at the N-terminal residue of the polypeptide, peptide or variant. Other amino-terminal modifications include aminooxypentane modifications (see Simmons et al., *Science* 276:276 (1997)).

In addition, the amino acid sequence of an Iss polypeptide can be modified so as to result in a specific polypeptide variant. The modification includes the substitution of at least one amino acid residue in the peptide for another amino acid residue, and includes substitutions that utilize the D rather than L form, as well as other well known amino acid analogs.

One or more residues of the polypeptide or peptide can be altered, so long as the resultant variant is biologically active. Conservative amino acid substitutions are preferred. For example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions within the scope of the invention include those shown in Table 2 under the heading of exemplary substitutions. More preferred substitutions are under the heading of preferred substitutions. After the substitutions are introduced, the resulting variants are screened for biological activity.

TABLE 2

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions polypeptide or peptide variants with non-conservative substitutions. Non-conservative substitutions entail exchanging a member of one of the classes described above for another.

Acid addition salts of the polypeptide, peptide or variant thereof or of amino residues of the polypeptide, peptide or variant may be prepared by contacting the polypeptide, peptide, variant or amine thereof with one or more equivalents of the desired inorganic or organic acid, such as, for example, hydrochloric acid. Esters of carboxyl groups of the polypeptides or peptides may also be prepared by any of the usual methods known in the art.

F. Preparaion of Iss Antibodies

The immunogenic Iss polypeptides or variants thereof prepared as described above are used to produce antibodies, including polyclonal and monoclonal. As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain (VH and VL, respectively), which form hyper-variable loops which contribute to antigen binding. The term antibody also includes, for example, vertebrate antibodies, hybrid antibodies, chimeric antibodies, altered antibodies, univalent antibodies, monoclonal and polyclonal antibodies, the Fab proteins and single domain antibodies.

If polyclonal antibodies are desired, a selected animal (e.g., mouse, rabbit, goat, horse or bird) is immunized with an immunogenic Iss polypeptide or Iss-fusion protein. Serum from the immunized animal is collected and treated according to known procedures. If serum containing polyclonal antibodies to an Iss antigen contains antibodies to other antigens, the polyclonal antibodies can be purified by immuno-affinity chromatography. Techniques for producing and processing polyclonal antisera are known in the art, see for example, Mayer and Walker eds. *Immunochemical Methods in Cell and Molecular Biology* (Academic Press, London) (1987).

Monoclonal antibodies directed against Iss antigens or polypeptides can be readily produced by one skilled in the art. The general methodology for making monoclonal antibodies by hybridomas is well known. Immortal antibody-producing cell lines can be created by cell fuision, and also by other techniques such as direct transformation of B lymphocytes with oncogenic DNA, or transfection with Epstein-Barr virus. See, e.g., Schreier et al. *Hybridoma Techniques*, (1980); Hammerling et al. *Monoclonal Antibodies and T-cell Hybridomas*, (1981); Kennett et al. *Monoclonal Antibodies* (1980); see also, U. S. Pat. Nos. 4,341, 761; 4,399,121; 4,427,783; 4,444,887; 4,466,917; 4,472, 500; 4,491,632; and 4,493,890. Panels of monoclonal antibodies produced against Iss antigens can be screened for various properties, for example, isotype, epitope affinity, etc.

Preferably, an Iss polypeptide, peptide, variant or subunit thereof, or Iss-fusion protein, is utilized to immunize mice for the preparation of monoclonal antibodies. If it is determined that an Iss polypeptide, a fragment or variant thereof does not elicit a strong humoral response in the immunized mice, a larger and possibly more immunogenic fusion protein (e.g., GST-Iss) can be used as an immunogen. However, regardless of the immunogen used, antibody specificity is determined using Iss alone. Briefly, antigen (an Iss polypeptide, variant or a fragment thereof, or GST-Iss) is emulsified in Complete Freund's Adjuvant and the emulsion used to immunize Balb/c mice (about 50–100 μg antigen per mouse given IP). Mice are boosted with an emulsion of antigen-Incomplete Freund's Adjuvant twice at about 10 day intervals (about 50–100 μg antigen each, given IP). About ten days after the second booster, an antigen-capture ELISA is run to determine the response of the mice to Iss.

The detection of antibody responses specific for the polypeptide can be used in ELISA-based immunoassays for the serodiagnosis of a septicemic disease or virulent, complement resistance *E. coli*. The ELISA is performed by using Iss to coat wells of microtiter plates. After overnight incubation, coated plates are washed thoroughly, and non-specific binding sites are blocked. After incubation, plates are thoroughly washed. The primary antibody, i.e. antibody contained in the sera from mice immunized with Iss or GST-Iss, is diluted and added to the microtiter plate wells. Following additional washes, a goat anti-mouse IgG- and IgM- alkaline phosphatase conjugate is added to the wells. After incubation and thorough washing, the substrate for the phosphatase, p-nitrophenyl phosphate, is added to the wells. Plates are incubated in the dark for about 10–45 minutes. Subsequently, changes in absorbance of the plate's contents are read at 405 nm with a microplate spectrophotometer as an indication of mouse response to Iss antigen. With the identification of a positive antibody, production of monoclonals can proceed. If a positive antibody is not identified, more boosters may be used, or techniques to increase the immunogenicity of Iss can be implemented as stated above. Alternatively, GST-Iss can be used as the immunogen.

Responding mice are given a final booster consisting of about 5–100 μg, preferably 25–50 μg of antigen, preferably without adjuvant, administered intravenously. Three to five days after final boosting, spleens and sera are harvested from all responding mice, and sera is retained for use in later screening procedures. Spleen cells are harvested by perfusion of the spleen with a syringe. Spleen cells are collected, washed, counted and the viability determined via a viability assay. Spleen and SP2/0 myeloma cells (ATCC, Rockville, Md.) that have been screened for HAT sensitivity and absence of bacterial contamination are combined, the suspension pelleted by centrifugation, and the cells fused using polyethylene glycol solution. The "fused" cells are resuspended in HT medium (RPMI supplemented with 20% fetal bovine serum (FBS), 100 units of penicillin per ml, 0.1 mg of streptomycin per ml, 100 μM hypoxanthine, 16 μM thymidine, 50 μM 2-mercaptoethanol and 30% myeloma-conditioned medium) and distributed into the wells of microtiter plates. Following overnight incubation at 37° C. in 5% $CO_2$, HAT selection medium (HT plus 4 μM aminopterin) is added to each well and the cells fed according to accepted procedures known in the art. In approximately 10 days, medium from wells containing visible cell growth are screened for specific antibody production by ELISA. Only wells containing hybridomas making antibody with specificity to Iss, or GST-Iss, are retained. The ELISA is performed as described above, except that the primary antibody added is contained in the hybridoma supernatants. Appropriate controls are included in each step.

This process generates several hybridomas producing monoclonal antibodies to Iss polypeptides, or an Iss-ftision protein, e.g., GST-Iss. Hybridoma cells from wells testing positive for anti-Iss, or anti-GST-Iss antibodies are cloned by limiting dilution and re-screened for anti-Iss antibody production using ELISA. Cells from positive wells are subcloned to ensure their monoclonal nature. The most reactive lines are then expanded in cell culture and samples are frozen in 90% FBS-10% dimethylsulfoxide. All monoclonal antibodies are characterized using a commercial isotyping kit (BioRad Isotyping Panel, Oakland, Calif.) and partially purified with ammonium sulfate precipitation followed by dialysis. Further purification is performed using protein-A affinity chromatography.

Antibodies, both monoclonal and polyclonal, that are directed against Iss antigens are particularly useful in diagnosis. Those that are neutralizing are useful in passive immunotherapy and treatment. Monoclonal antibodies, in particular, may be used to raise anti-idiotype antibodies.

The term "treatment," as used herein, refers to prophylaxis and/or therapy of an avian subject diagnosed with, exhibiting characteristics or symptoms of, various *E. coli* infections including, but not limited to, colibacillosis, coligranuloma, peritonitis, salpingitis, synovitis, omphalitis and air sacculitis. The term "therapy" refers to providing therapeutic benefit or effect to an avian subject such that the subject exhibits few or no symptoms of a septicemic disease or other related diseases. Such treatment can be accomplished by administration of nucleic acids, polypeptides or antibodies of the instant invention.

G. Preparation of Immunogenic Compositions and Vaccines of the Invention

The preparation of immunogenic compositions or vaccines that contain immunogenic polypeptide(s), peptides, and polypeptides encoded by the nucleic acid molecules of the invention as an active ingredient are known to one skilled in the art. As used herein, the term "immunogenic composition" refers to a composition or preparation administered in an amount effective to raise antibodies in a recipient and further provides some therapeutic benefit or effect so as to result in an immune response that inhibits or prevents a septicemic disease in avian, or so as to result in the production of antibodies to a virulent complement resistant avian *E. coli* isolate, or polypeptide or peptide employed as an immunogen. Both local and systemic administration is contemplated. Systemic administration is preferred.

The term "vaccine" refers to the process of immunization and the administration of an antigen or a suspension of antigens, derived from either bacteria or viruses, that upon administration, will produce active immunity and provide protection against those viruses or bacteria or related viruses or bacteria, utilizing either conventional, traditional or recombinant techniques, e.g. those involving recombinant DNA technology or synthetic peptides. Typically, such immunogenic compositions and vaccines are prepared as injectables, either as liquid solutions or suspensions. Solid forms suitable for solution in, or suspension in, liquid prior to injection may also be prepared. The preparation may also be emulsified, or the polypeptide encapsulated in liposomes.

The active immunogenic ingredients are often mixed with excipients or diluents that are pharmaceutically acceptable as carriers and compatible with the active ingredient. The term "pharmaceutically acceptable carrier" refers to a carrier (s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the immunogenic composition or vaccine may contain minor amounts of auxiliary substances such as wetting or emulsifying agents, pH buffering agents, and/or adjuvants which enhance the effectiveness of the immunogenic composition or vaccine.

Examples of adjuvants or carriers that may be effective include but are not limited to: aluminum hydroxide, N-acetyl-muramyl-L-threonyl-D-isoglutamine (thr-MDP); N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalnitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL +TDM +CWS) in a 2% squalene/Tween 80 emulsion. The effectiveness of an adjuvant may be determined by measuring the amount of antibodies directed against an immunogenic polypeptide containing an Iss antigenic sequence resulting from administration of the polypeptide in immunogenic compositions or vaccines that are also comprised of the various adjuvants.

H. Dosages, Formulations and Routes of Administration of Nucleic Acid Molecules and Polypeptides of the Invention The nucleic acid molecules, polypeptides or peptides of the invention are preferably administered to an avian subject so as to result in an immune response specific for the polypeptide, including the polypeptide encoded by the nucleic acid molecules of the invention or peptide. The immunogenic compositions and vaccines of the present invention are conventionally administered parenterally, by injection, for example, either subcutaneously or intramuscularly either as liquid solutions or suspensions. Solid forms suitable for suspension in a liquid vehicle prior to injection or infusion can also be prepared. Additional formulations that are suitable for administration include oral formulations. Oral formulations include such normally employed excipients as, for example, pharmaceutical grades of mannitol, lactose, starch, magnesium stearate, sodium saccharine, cellulose, magnesium carbonate and the like. Iss polypeptides may be formulated into an immunogenic composition or vaccine as neutral or salt forms. These compositions take the form of solutions, suspensions, tablets, pills, capsules, sustained release formulations or powders and contain about 10%–95% of active ingredient, preferably about 25%–70%.

Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides and such organic bases as isopropylamine, trimethylamine, ethylamino ethanol, histidine, procaine, and the like.

Immunogenic compositions and vaccines comprising nucleic acid molecules, polypeptides or peptides of the instant invention, are administered to an animal, e.g., chicken, turkey, and other avian subjects, in a manner compatible with the dosage formulation, and in such amount as will be prophylactically and/or therapeutically effective and result in an immune response that is specific for an Iss polypeptide, Iss peptide, or Iss polypeptide encoded by a nucleic acid molecule. It is very common to express dosage units in mg/kg (i.e., mg/kg of body weight) or, if a continuing series of doses over many days is contemplated, mg/kg/ day. An immunogenic composition or vaccine of the invention will usually contain an effective amount, e.g., an amount capable of eliciting an immune response in an avian subject, of an Iss polypeptide in conjunction with a conventional, pharmaceutically acceptable carrier. The dosage will vary depending upon the specific purpose for which the protein is being administered. The prepared compounds and compositions can be administered to avian subjects for veterinary use, such as for use with domestic or farm animals.

In general, the dosage required for efficacy will range from about 0.003 to 100 mg/kg, preferably about 0.05 to 50 mg/kg, and more preferably 0.5 to 30 mg/kg, although other dosages can provide beneficial effects. A dosing method as described in Borch et al. U.S. Pat. No. 5,035,878, provides additional guidance. Although Borch et al. is directed to mammals, the weight of an avian subject can readily be substituted. Dosage, however, may depend on the avian subject to be treated, capacity of the avian subject's immune system to synthesize antibodies, and the degree of protection desired. Precise amounts of active ingredient required to be administered may depend on the judgment of the practitioner and may be peculiar to the avian subject to be immunized.

The immunogenic composition or vaccine can be given in a single dose schedule, or preferably in a multiple dose schedule. A multiple dose schedule is one in which a primary course of vaccination may be with approximately 1–10 separate doses, followed by other doses given at subsequent time intervals required to maintain and or reenforce the immune response, for example, at about 1–4 months for a second dose, and if needed, a subsequent dose(s) after several months. The dosage regimen will also, at least in part, be determined by the need of the avian subject and be dependent upon the judgment of the practitioner. In addition, the immunogenic composition or vaccine containing an immunogenic Iss antigen(s), Iss polypeptide or Iss fusion polypeptide can be administered in conjunction with other immunoregulatory agents, for example, immune globulins.

Administration of sense or antisense nucleic acid molecules can be accomplished through the introduction of cells transformed with an expression vector, as described above, comprising the nucleic acid molecule (see for example, WO 93/02556) or the administration of the nucleic acid molecule (see, for example, Felgner et al., U.S. Pat. No. 5,580, 859, Pardoll et al., *Immunity* 3:165 (1995); Stevenson et al., *Immunol. Rev.* 145:211 (1995); Molling, *J. Mol. Med.* 75:242 (1997); Donnelly et al., *Ann. N.Y. Acad. Sci.* 772:40 (1995); Yang et al., *Mol. Med. Today* 2:476 (1996); Abdallah et al., *Biol. Cell* 85:1 (1995)). Pharmaceutical formulations, dosages and routes of administration for nucleic acids are generally disclosed, for example, in Felgner et al., and are fully applicable to avian subjects.

I. Immunoassay and Diagnostic Kits

Polypeptides that react immunologically with serum containing Iss antibodies or Iss-fusion protein antibodies are useful in immunoassays to detect presence of avian *E. coli* Iss in biological samples. Examples of useful antibodies include those derived from, expressed from, or encoded within the Iss clones described in Example 1, and composites thereof, and the antibodies raised against the Iss antigens in these polypeptides.

Design of an immunoassay is subject to a great deal of variation, and many formats are known in the art. Ideally the immunoassay will utilize at least one antigen derived from an avian *E. coli* Iss. In one embodiment, the immunoassay can utilize a combination of antigens derived from Iss or an Iss fusion polypeptide. These antigens can be derived from the same or from different Iss polypeptides, and may be in separate recombinant or natural polypeptides, or together in the same recombinant polypeptides.

An immunoassay may use, for example, a monoclonal antibody directed towards an Iss antigen(s) or Iss fusion polypeptide, a combination of monoclonal antibodies directed towards several Iss antigens or Iss fusion polypeptides, polyclonal antibodies directed towards the same Iss antigen or Iss fusion polypeptide, or polyclonal antibodies directed towards different Iss antigens or Iss fusion polypeptides. Protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, enzymatic, fluorescent, chemiluminescent, radioactive, or dye molecules. Assays which amplify the signals from the probe are also known. Examples of these are assays that utilize biotin and avidin, and enzyme-labeled and mediated immunoassays, such as ELISA assays.

Typically, an immunoassay for an anti-Iss antibody(s) will involve selecting and preparing the test sample suspected of containing the antibodies, such as a biological sample, then incubating it with an antigenic (i.e., epitope-containing) Iss polypeptide(s) or Iss fusion polypeptide(s) under conditions that allow antigen-antibody complexes to form, and then detecting the formation of such complexes. Suitable incubation conditions are well known in the art. The immunoassay may be, without limitation, in a heterogeneous or in a homogeneous format and of a standard or competitive type.

In a heterogeneous format, the polypeptide is typically bound to a solid support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylindine fluoride (known as lmmulon™)), diazotized paper, nylon membranes, activated beads and Protein A beads. For example, Dynatech Immulon™ 1 or Imnulon™ 2 microtiter plates or 0.25 inch polystyrene beads (Precision Plastic Ball) can be used in the heterogeneous format. The solid support containing the antigenic polypeptide is typically washed after separating it from the test sample, and prior to detection of bound antibodies. Both standard and competitive formats are known in the art.

In a homogeneous format, the test sample is incubated with antigen in solution. For example, it may be incubated under conditions that will precipitate any antigen-antibody complexes that are formed. Both standard and competitive formats for these assays are known in the art.

In a standard format, the amount of Iss antibodies forming the antibody-antigen complex is directly monitored. This may be accomplished by determining whether labeled anti-xenogenic antibodies that recognize an antigen on anti-Iss antibodies will bind due to complex formation. In a competitive format, the amount of Iss antibodies in the sample is deduced by monitoring the competitive effect on the binding of a known amount of labeled antibody (or other competing ligand) in the complex.

Complexes formed comprising anti-Iss antibody (or, in the case of competitive assays, the amount of competing antibody) are detected by any of a number of known techniques, depending on the format. For example, unlabeled Iss antibodies in the complex may be detected using a conjugate of anti-xenogenic Ig complexed with a label, (e.g., an enzyme label).

In immunoassays where Iss polypeptides are the analyte, the test sample, typically a biological sample, is incubated with anti-Iss antibodies under conditions that allow the formation of antigen-antibody complexes. Various formats can be employed. For example, a "sandwich assay" may be employed, where antibody bound to a solid support is incubated with the test sample; washed; incubated with a second, labeled antibody to the analyte, and the support is washed again. Analyte is detected by determining if the second antibody is bound to the support. In a competitive format, which can be either heterogeneous or homogeneous, a test sample is usually incubated with antibody and a labeled, competing antigen is also incubated, either sequentially or simultaneously. These and other formats are well known in the art.

Kits suitable for immunodiagnosis and containing the appropriate labeled reagents are constructed by packaging the appropriate materials. These kits include the polypeptides of the invention containing Iss antigens, or antibodies directed against Iss epitopes, in suitable containers, along with the remaining reagents and materials required for the conduct of the assay packaged in preselected amounts, as well as a suitable set of assay directions. All of these items are contained within the outer packaging of the kit, which may be a box, envelope, or the like. The assay directions preferably comprises instruction means such as a printed insert, a label, a tag, a cassette tape and the like, instructing the user in the practice of the assay format.

Additionally, iss probes can be packaged into diagnostic kits. Such diagnostic kits can include avian *E. coli* iss nucleic acid probe(s), that may be labeled. As used herein, the term "probe" refers to a polynucleotide that forms a hybrid structure with a sequence in a target region, due to complementarity of at least one sequence in the probe with a sequence in the target region. Specifically a probe is a nucleic acid sequence between 10 and 500 base pairs in length that contains specific nucleotide sequences that specifically and preferentially hybridize under predetermined conditions to nucleic acid sequences of an avian *E. coli* iss nucleic acid sequence.

Alternatively, the probe DNA may be unlabeled and the ingredients for labeling the probe may be included in separate containers in the kit. The kit may also contain other suitably packaged reagents and materials needed for the particular hybridization protocol (e.g., standards) as well as instructions for conducting the test.

For example, one such diagnostic kit for detecting or determining antibodies to Iss or an Iss fusion polypeptide comprises packaging containing, separately packaged: (a) a solid surface, such as a fibrous test strip, a multi-well microtiter plate, a test tube, or beads, having bound thereto a polypeptide, peptide, variant, or subunit, of SEQ ID NO. 2 and (b) labeled anti-avian immunoglobulin. A second embodiment of a diagnostic kit for detecting or determining Iss comprises packaging containing, separately packaged: (a) a solid surface having bound thereto antibodies to the polypeptide of SEQ ID NO. 2 or a fragment thereof; and (b) a known amount of (i) antibodies specific to Iss or an Iss fusion polypeptide or (ii) antibodies to Iss that comprise a detectable label, or a binding site for a detectable label. A third embodiment of a diagnostic kit for detecting Iss or an Iss fusion polypeptide can comprise, in packaged association, separately packaged amounts of: (a) an Iss-specific antibody; (b) the labeled polypeptide of SEQ ID NO. 2 or a fragment thereof, and (c) an anti-avian immunoglobulin.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The following examples are intended to illustrate but not limit the invention.

EXAMPLE 1

Identification, cloning and sequence of an avian *E. coli* iss gene

A wild-type *E. coli* isolate was obtained from the serum of a chick with systemic colibacillosis. The isolate was identified as an O2 serotype. The virulence of the isolate was determined by embryo lethality assay. Twelve-day-old embryonated eggs were obtained from Seaboard, Athens, Georgia. Overnight cultures of the isolates that were tested, including virulent and avirulent control organisms, were pelleted by centrifugation, washed twice in phosphate-buffered saline (1×PBS) and resuspended to a concentration of $10^2$ colony-forming units per 0.10 ml of PBS. The final concentration was then confirmed by viable counts. The 0.1-ml inoculum was then injected into the allantoic cavity of each embryo. Twenty embryos per isolate were utilized. Inoculated embryos were incubated at 37° C. and counted daily for 4 days to identify dead embryos (Minshew et al., *Infect Immun.* 20:50–54 (1978); Nolan et al., *Avian Dis.* 36:395–397 (1992)).

Inoculation of the isolate into chick embryos resulted in death of 98% of the embryos, indicating that the isolate was virulent. The isolate also was resistant to the lytic effects of complement, which did not degrade C3, and limited C3 deposition on the cell surface of the bacterium when compared with a complement-sensitive mutant of this wild-type isolate.

The isolate contained several plasmids including a 100-kb plasmid that produced Colicin V. The isolate also produced the siderophores, enterobactin and aerobactin. The isolate was non-hemolytic on blood agar (Nolan et al., *Avian Dis.*, 36:398–402 (1992)), motile (Nolan et al., *Avian Dis.*, 36:395–397 (1992)), and lacked K1 antigen, capsule, and type I pili. Additionally, the isolate contained the traT(Nolan et al., *Avian Dis.*, 3:146–150 (1994)) and iss genes, had a smooth LPS (Nolan et al., *Avian Dis.*, 38:146–150 (1994)), was resistant to rough-specific bacteriophages (Nolan et al., *Avian Dis.*, 38:146–150 (1994)) and to the antibiotics, streptomycin, sulfisoxazole and tetracycline.

The complete iss gene from this isolate was obtained by PCR amplification utilizing the following oligonucleotide primer pair:

5'-GTGGCGAAAACTAGTAAAACAGC-3' (SEQ ID NO.3) and

5'-CGCCTCGGGGTGGATAA-3' (SEQ ID NO.4).

The primer pair was selected using DNASTAR's Primer Select Program (Madison, Wis.). The resultant 760 bp PCR product (SEQ ID NO.1) was sequenced and cloned into a pGEM-T vector (Promega Corp., Madison, Wis.) (Sambrook, Fitsch & Maniatis, *Molecular Cloning*; A Laboratory Manual, Cold Spring Harbor Laboratory Press (1989); DNA Cloning, Volumes I and II (D. N. Glover ed. 1985)). The resulting iss plasmid clones were also sequenced to confirm their identities using standard procedures with a LICORT automated sequencer (Lincoln, Nebr.). The iss DNA sequence was compared with the iss sequence from an isolate of a human *E. coli* and the sequence of lambda bor (Barondess et al., *J. Bacteriol.*, 177:1247–1253 (1995); Barondess et al., *Nature*, 346:871–874 (1990); Chuba et al., *Mol. Gen. Genet.*, 216:287–292 (1989)) using Lasergene Software (DNASTAR) and FASTA (EMBL, Heidelberg, Germany). The DNA sequence alignment of those three genes is shown in FIG. 1. The avian *E. coli* iss sequence was submitted to GENBANK on Jan. 10, 1998, and has been assigned accession number AF042279.

EXAMPLE 2

Expression of Iss

Two amplified iss sequences, one containing a full-length iss sequence as shown in FIG. 1 (SEQ ID NO.1), and the other containing a truncated iss sequence wherein nucleotides 1–72 (FIG. 1) were deleted, were cloned in frame into the expression vector, pGEX-6P-3 (Pharmacia Biotech Inc., Piscataway, N.J.), generating plasmid clones pLN321 and pLN322 respectively. The pGEX-6P-3 vector was used in combination with a GST Gene Fusion System Purification Kit (Pharmacia Biotech Inc., Piscataway, N.J.) and provided a complete system for expressing and purifying resulting Iss polypeptides.

Once cloned into the pGEX-6P-3 expression vector, both plasmid clones were sequenced and shown, by DNA sequencing, to be fused to the GST vector in the proper reading frame (FIG. 3, showing pLN321 only). The pLN321 construct was then used to transform a protease-deficient *E. coli* strain BL21 (Pharmacia Biotech Inc., Piscataway, N.J.). Protein expression was induced with IPTG (Pharmacia Biotech Inc., Piscataway, N.J.). Following induction, the *E. coli* were lysed and the lysates were analyzed by SDS-PAGE. The crude total protein preparations showed that the uninduced and induced *E. coli* containing these constructs differed in their expression of a 37-kD protein band (FIG. 4). The 37-kD band, lane 3I of FIG. 4, corresponds in size to the predicted Glutathione S-Transferase-Iss (GST-Iss) fusion protein, as the Iss polypeptide has a molecular weight of approximately 10–11 kD, and GST has a molecular weight of approximately 26 kD. The 37-kD product obtained from the iss-pGEX-6P-3 construct, was found in the induced bacterial lysate, and not in the uninduced lysate.

Figure 5:
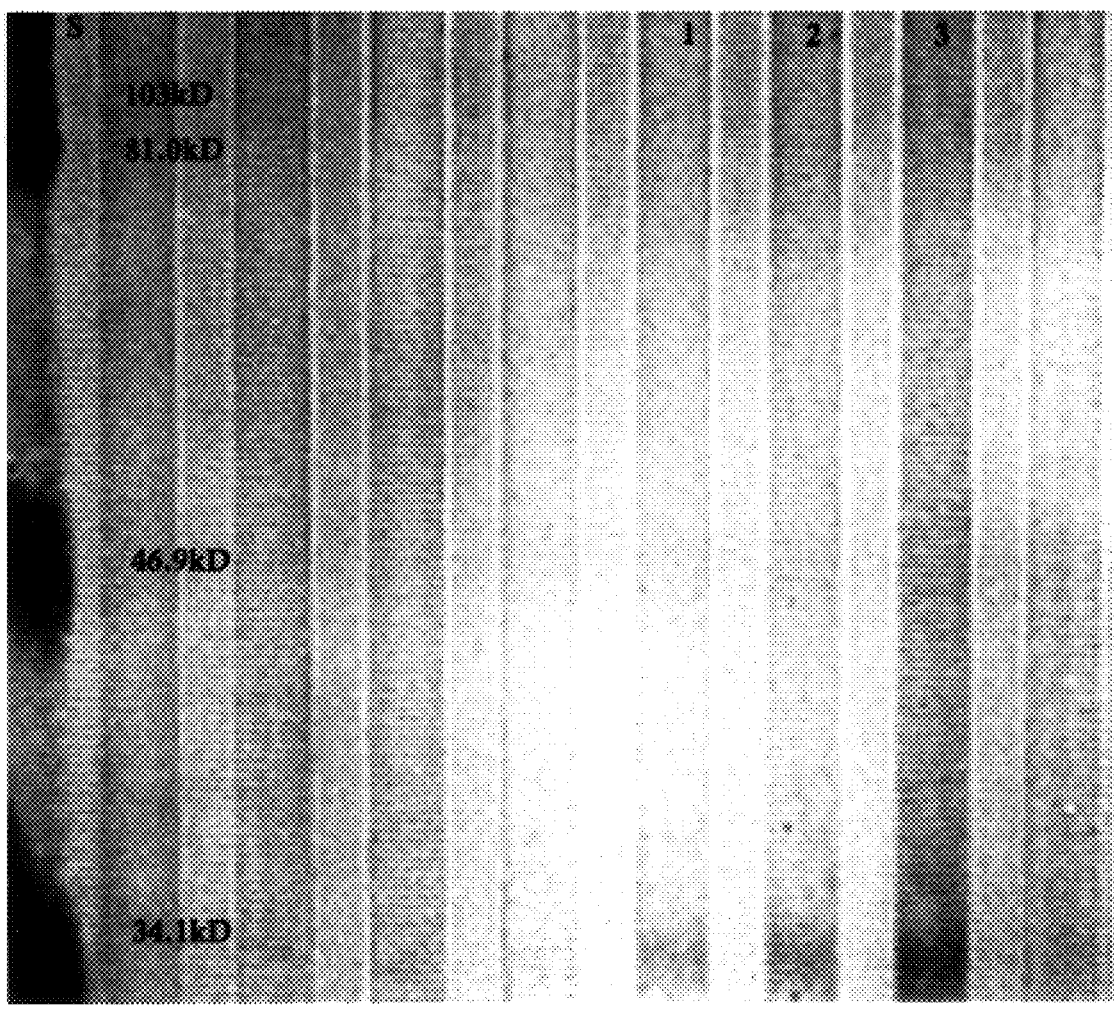
FIG. 5 shows the crude total protein preparation of a protease-deficient *E. coli*, containing pGEX-6P-3 comprising the iss gene sequence. Total protein was prepared 3 hours post-induction of expression with IPTG. After resolution by SDS-PAGE, the proteins were transferred to PVDF and the blot probed with anti-GST. Lane S=molecular weight standard in kD; Lanes 1, 2 and 3 =contain the same amount of crude bacterial lysate but different concentrations of anti-GST (e.g, base solution of 5/mg/ml diluted to 1:500 (lane 3), 1:1000 (lane 2) and 1:2000 (lane 1)). In a second PVDF blot using crude lysates of uninduced bacteria that was probed in a technique as described above, no bands were recognized (not shown), thus confirming the 37-kD band present in induced bacteria is the GST-Iss fusion protein.

To further confirm the identity of the 37-kD band observed in the induced bacterial lysate, the proteins of these lysates were transferred from the SDS-PAGE gel to a PVDF membrane (BioRad, Oakland, Calif.). The PVDF membrane was then probed with a GST monoclonal antibody (Pharmacia Biotech Inc., Piscataway, N.J.)). After washing, bound antibody was detected using a secondary antibody conjugated to alkaline phosphatase in the presence of the color reagent, BCIP/NBT enzyme substrate (BioRad, Oakland, Calif.). The 37-kD band was recognized by anti-GST, thereby confirming that the 37-kD band represented a GST-Iss fusion product (FIG. 5).

EXAMPLE 3

Purification and isolation of Iss

Polypeptides prepared from the pGEX-6P-3 expression vector yielded a glutathione S-transferase-Iss ("GST-Iss") fusion polypeptide product that is readily purified from the bacterial lysates by affinity chromatography under mild, non-denaturing conditions. Specifically, a bacterial sonicate is applied to a column of glutathione sepharose 4B at 4° C. and washed three times with 10 bed volumes of 1×PBS. Glutathione elution buffer (10 mM reduced glutathione in 50 mM Tris-HCl (pH 8.0)) is added to the column and incubated at room temperature (about 22–25° C.) for 10 minutes, and the fusion protein is eluted. Eluates recovered from the column contain the fusion protein.

Alternatively, after expression of GST-Iss in *E. coli*, the bacteria are lysed by sonication, and the insoluble material is pelleted and removed, and the supernatant passed through a slurry of Glutathione Sepharose 4B (Pharmacia Biotech Inc., Piscataway, N.J.) to permit binding of the GST-Iss fusion polypeptide to the Sepharose beads. To remove GST-Iss from other cellular proteins, the "bead-bound" fusion polypeptide is pelleted by centrifugation and washed with 1×PBS. The desired product is eluted from the Sepharose by the addition of reduced glutathione (Pharmacia Biotech Inc., Piscataway, N.J.). Upon removal from the Sepharose beads, the purified GST-Iss fusion product is cleaved into Iss and GST by a site-specific protease, such as PreScission Protease (Pharmacia Biotech Inc., Piscataway, N.J.), and the remaining GST is separated from Iss by the same procedure used to purify the GST-Iss fusion polypeptide. The resulting polypeptide products are then analyzed by SDS-PAGE.

EXAMPLE 4

Presence of iss in avian *E. coli* isolates

Two hundred and ten *E. coli* isolates from poultry clinically diagnosed with colibacillosis were obtained from several locations in the United States. Fifty-six *E. coli* isolates from the feces of apparently healthy poultry were obtained from the University of Georgia or were from poultry in North Dakota. The identity of all E. coli isolates was confirmed using API20E Strips (bioMerieux, Vitek, Inc., Hazelwood, Mo.). Non-*E. coli* strains (Table 3) used to evaluate the specificity of the probes were obtained from the NDSU Veterinary Diagnostic Laboratory.

TABLE 3

| | |
|---|---|
| *Bacillus subtilis* | *Micrococcus luteus* |
| *Citrobacter freundii* | *Proteus mirabilis* |
| *Enterobacter aerogenes* | *Pseudomonasfluorescens* |
| *Enterobacter cloacae* | *Rhodococcus erythropolis* |
| *Hafria alvei* | *Staphylococcus aureus* |
| *Klebsiella oxytoca* | *Staphylococcus epidermidis* |
| *Klebsiella pneumoniae* | *Streptococcus faecalis* |
| *Salmonella typhimurium* (Copenhagen) | |

All isolates were maintained in LB broth (Difco Laboratories, Detroit, Mich.) supplemented with 20% glycerol and stored at −70° C. prior to use. When subjected to total DNA isolation procedures, sample isolates were grown in BHI (Difco Laboratories, Detroit, Mich.), with or without antibiotics, overnight at 37° C. In preparation for amplification procedures, isolates were grown on MacConkey agar (Difco Laboratories, Detroit, Mich.) overnight at 37° C. For colony blotting procedures, test organisms were grown on LB agar (Difco Laboratories, Detroit, Mich.) overnight at 37° C.

Probe Construction

A cvaC probe was prepared by digesting plasmid pHK11 (Dr. R. E. Wooley, University of Georgia, Athens, Ga.) with the restriction enzymes EcoRI and BglII, which were obtained from Promega Corp. (Madison, Wis.) to yield a 1.9 kb fragment (Gilson et al., *J. Bacteriol.* 169:1466–2470 (1987)). To obtain a traT probe (Moll et al., *Infect. Immun.*, 2:359–367 (1980); Montenegro et al., *J. Gen. Microbiol.*, 131:1511–1521 (1985)), the plasrnid pKT107 (Dr. F. C.

Cabello, New York Medical College, Valhalla, N.Y.) was digested with BstEII to yield a 700 bp fragment.

Gene probes for ompA and iss were generated through DNA amplification techniques. Primer sequences useful to amplify ompA and iss sequences were selected using Lasergene software (DNAStar, Inc., Madison, Wis.) based on published sequences for these genes (Beck et al., Nuc. Acids Res., 8:3011–3024 (1980); Chuba et al., Mol. Gen. Genet., 216:287–292 (1989)) and were obtained from Genosys Biotechnologies, Inc., The Woodlands, Tex. Primers employed in the detection of ompA and iss are shown in Table 4.

TABLE 4

| Name | Sequences (5' to 3') | SEQ ID NO. | Tm |
|---|---|---|---|
| ompA | | | |
| upper primer | CTTGCGGAGGCTTGTCTGAG | 9 | 54.9° C. |
| lower primer | AGGCATTGCTGGGTAAGGAA | 10 | 53.7° C. |
| iss | | | |
| upper primer | GTGGCGAAAACTAGTAAAACAGC | 3 | 52.1° C. |
| lower primer | CGCCTCGGGGTGGATAA | 4 | 53.9° C. |
| iss | | | |
| issupper1ex | AAAGGGGATCCATGCAGGATAATAAGATGAAAAA | 11 | 73.6° C. |
| issupper73ex | CACAGGGATCCCAAACGTTTACTGTTGGAAACAA | 12 | 77.8° C. |
| isslower338ex | CGCCGGAATTCGCAGATGAGCTCCCCATATC | 13 | 82.4° C. |
| issupperdiag | ATGCAGGATAATAAGATGAAAAA | 14 | 47.6° C. |
| isslowerdiag | ATAGATGCCAAAAGTGATAAAAC | 15 | 47.2° C. | ompA and iss sequences were amplified according to the following procedure. A single colony of an E. coli isolate was transferred into 20 μl of Gene Releaser™ (Bioventures, Inc., Murfeesboro, Tenn.) and subjected to microwaves on the high setting for approximately 6 minutes (Kenmore, ultra-defrost). A PCR master mix consisting of 47.5 μl of $H_2O$, 10.0 μl of 10×PCR Buffer II (Perkin Elmer, Branchburg, N.J.), 16.0 μl of 1.25 mM dNTP mix (Promega), 0.5 μl of Taq DNA Polymerase (Promega, Madison, Wis.), 1.0 μl of 0.1 mM of each primer, and 4.0 μl of 25 mM $MgCl_2$ was added to an E. coli-Gene Releaser™ suspension. Amplification was performed according to the following parameters: 2 minutes at 97° C.; 1 minute at 97° C.; 1 minute at 49° C., 1 minute at 72° C. for 9 cycles; 1 minute at 95° C., 1 minute at 49° C., 1 minute at 72° C. for 24 cycles; 5 minutes at 72° C. and then the sample is maintained at 4° C.

Restriction enzyme digest plasmid fragments and amplification products were separated by horizontal gel electrophoresis. Amplified fragments were identified by size, excised from the agarose and purified using GENECLEAN™ (Bio101, La Jolla, Calif.) or the Wizard PCR Clean-Up System (Promega, Madison, Wis.). The identities of the amplicons were further confirmed by sequencing according to the procedures described below. To prepare probes, isolated fragments were labeled using a non-radioactive, random-primed DNA labeling kit (Genius I Labeling and Detection Kit, Boehringer Mannheim, Indianapolis, Ind.).

Sequencing of Amplified DNA

Sequencing was performed according to the manufacturer's protocol using the LI-COR 4000LR Automated DNA Sequencer (Lincoln, Nebr.). Briefly, 9 μl of each purified PCR product, containing 0.1 to 0.6 pmol DNA, was added to 2 μl of 1 pmol/μl of the appropriate primer DNA (for example, SEQ ID NOs: 3, 4, 9 and 10 in Table 4) 1.0 μl of dNTP mix, 1.0 μl of IRD40-dATP at 20 pmol/μl (Boehringer Mannheim, Indianapolis, Ind.), 2.5 μl of 10× Sequitherm™ Reaction Buffer (Epicentre Technologies, Madison, Wis.), and 1.5 μl of Sequitherm™ DNA Polymerase at 5 u/μl (Epicentre, Madison, Wis.). All components were mixed carefully in labeled tubes and covered with mineral oil. The tubes containing this mixture were placed in the thermal controller, and the cycle sequencing reaction was run as described in LI-COR (Lincoln, Nebr.) application bulletin 41.

The first series of cycles were the labeling reactions, wherein an IRD40-DATP was added to the extended primer sequence. The second series of cycles was the termination reaction for which 4 μl of the labeling reaction was added to 2 μl of each ddNTP termination mix before cycling. Unincorporated label was removed from the products by ethanol precipitation according to manufacturer's directions. Samples were separated on 4.0% Long Ranger acrylamide gels (FMC, Rockland, Me.) and analyzed via a LI-COR 4000 LR automated sequencer.

Amplification for Cloning ompA and iss sequences used for cloning were amplified according to the following procedure. A single colony of E. coli isolate was transferred into 20 μl of Gene Releaser™ (Bioventures, Inc., Murfeesburo, Tenn.) and subjected to microwaves on the high setting for approximately 6 minutes (Kenmore, ultra-defrost). Alternatively, a colony was transferred into 40 μl SCLB (10 mM Tris-HCl pH 7.5/1 mM EDTA/50 μg/ml proteinase K), and heated at 55° C. for 10 minutes, then heated at 80° C. for 10 minutes, diluted with 80 μl $ddH_2O$, cell debris was pelleted and 10 μl of the supernatant was used.

The prepared E. coli DNA was added to a master mix consisting of 47.5–53.5 μl $ddH_2O$, 10.0 μl of 10×PCR Buffer II (Perkin Elmer or Promega, Madison, Wis.), 0.5 μl of Amplitaq DNA polymerase (Perkin Elmer), 1.0 μl of 0.1 mM of each appropriate primer and 4.0 μl or 8.0 μl of 25 mM $MgCl_2$.

The amplification cycles were as previously described except that the annealing temperature was 49° C. or 51.8° C. depending on the primer pair used. Amplified fragments for ligation into the expression vector pGEX-6P-3, were digested with BamHI and EcoRI to produce sticky ends for the ligation process. Amplified fragments for ligation into pGEM-T vector have "A" overhangs left by Taq polymerase. Restriction enzyme digest plasmid fragments and amplification products were separated by horizontal gel electrophoresis. Amplified fragments were identified by size, excised from the agarose and purified using the Wizard PCR Clean-Up System (Promega, Madison, Wis.). T7 DNA ligase was used to ligate amplification fragments into the vectors. The identities of the amplicons were further confirmed by sequencing according to the procedures described below.

Sequencing of Cloned DNA

Sequencing was performed according to the manufacturer's protocol using the LI-COR 400OLR Automated DNA Sequencer (Lincoln, Nebr.). Briefly, 9 μl of each purified plasmid clone containing 0.2 to 0.6 pmol DNA, was added to 1 μl of 1 pmol/μl IRD41 labeled primer DNA (Table 5), 2.5 μl of 10× Sequitherm™ Reaction Buffer (Epicentre Technologies, Madison, Wis.), and 1.0 μl of Sequitherm™ DNA Polymerase at 5 u/μl (Epicentre, Madison, Wis.) and 2.5 μl ddH$_2$O. All components were mixed carefully before 4 μl were aliquoted to 2 μl of each ddNTP termination mix in labeled tubes and covered with mineral oil. The tubes containing this mixture were placed in the thermal controller, and the cycle sequencing reaction was run as described in LI-COR (Lincoln, Nebr.) application bulletin 13. Samples were separated on 4.0% acrylamide gels and analyzed via a LI-COR 4000 LR automated sequencer.

TABLE 5

| Name | Sequences (5' to 3') | SEQ ID NO. |
|---|---|---|
| M13 Forward (−29)/IRD41 Dye-labeled primer | CACGACGTTGTAAAACGAC | 16 |
| M13 Reverse IRD41 Dye-labeled primer | GGATAACAATTTCACACAGG | 17 |
| 5'pGEX IRD41 Dye-labeled sequencing primer | GGGCTGGCAAGCCACGTTTGGTG | 18 |
| 3'pGEX IRD41 Dye-labeled sequencing primer | CCGGGAGCTGCATGTQTCAGAGG | 19 |

Colony Blotting

Isolates were stab-inoculated into LB agar and incubated overnight at 37° C. Table 3 indicates positive and negative control organisms. Colonies were transferred to charge-modified nylon membranes (QIABRANE Nylon Plus membrane, QIAGEN, Inc., Chatsworth, Calif.) by the method of Grunstein and Hogness (Grunstein et al., *Proc. Natl. Acad. Sci.* (USA), 72:3961–3065 (1975)). The colonies were lysed and the DNA denatured. Membranes were then stored and sealed in plastic bags (GibcoBRL, Gaithersburg, Md.) at 4° C.

Total DNA Isolation and Blotting

Total DNA from all test isolates, including non-*E. coli* strains and control organisms, were isolated by the method of Marmur, *J. Mo. Biol.*, 3:208–218 (1961). Briefly, individual isolates were grown overnight at 37° C. with agitation in 50 ml of BHI. Cultures were pelleted by centrifugation (15 minutes at 5000×g) and the pellets were resuspended in 5 ml of BPES buffer (10 mM HPO$_4$, 0.2 M NaCl$_2$, and 1 mM EDTA, pH 8.0). Five mg of lysozyme (Sigma Chemical Co., St. Louis, Mo.) was added to each suspension and incubated for 45 minutes at 37° C. with gentle agitation prior to addition of 0.1 ml of 25% SDS and 1.0 ml of 5 M sodium perchlorate (Sigma). Suspensions were then incubated for 15 minutes at 65° C. with occasional swirling, cooled to room temperature, and 6.5 ml of chloroform isoamyl alcohol (24:1) (Amresco, Solon, Ohio) was added to each suspension. Tubes were shaken for 5 minutes, and the suspensions pelleted by centrifugation (10 minutes at 600×g). The aqueous phase was removed to a glass beaker containing two volumes of cold absolute ethanol. Sterile glass rods were used to spool the DNA, which was put into 25 ml plastic, screw-top centrifuge tubes (Fisher Scientific, Chicago, Ill.). These tubes were centrifuged for 10 minutes at 700×g, the ethanol decanted, and the DNA allowed to dry. DNA was resuspended in sterile 1×TE buffer (100 mM Tris-Cl, 10 mM EDTA pH 8.0) (5 Prime→3 Prime, Inc. Boulder, Colo.).

Samples of total DNA from each organism were spotted onto nylon, the spots allowed to dry, and the DNA denatured in Denaturation Solution (5 Prime→3 Prime, Inc., Boulder, Colo.) for 15 minutes. These "dot" blot membranes were dried briefly on filter paper and were put in Neutralization Solution (5 Prime→3 Prime, Inc., Boulder, Colo.) for 15 minutes. Membranes were then placed on filter paper saturated with 2×SSC (pH 7.0; 5 Prime - 3 Prime, Inc., Boulder, Colo.) for 5 minutes. All filters were stored in sealed plastic bags (Gibco BRL) at 4° C.

Hybridization Studies

Membranes were prehybridized in aqueous solution (Prehybridization Solution, 5 Prime→3 Prime, Inc.) for 4 hours at 68° C. and hybridized with the individual, denatured probes at 68° C. for 12 hours (Russo et al., *Infect. Immun.* 61:3578–3582 (1993)). The filters were given two 1 hour washes in 0.1×SSC (5 Prime→3 Prime, Inc., Boulder, Colo.) with 0.1% SDS (Sigma Chemical Co., St. Louis, Mo.). Hybridized probes were detected using the protocol in the Genius 1 kit (Sambrook, Fitsch & Maniatis, *Molecular Cloning*; A Laboratory Manual, Cold Spring Harbor Laboratory Press; pp 9.34–9.55 (1989)).

Capsule Staining

All isolates were examined for the presence of capsule using the method of Hiss, P. H. Jr., *J. Exp. Med.* 6:317:345 (1905). Briefly, a loopful of normal horse serum was mixed with a loopful of overnight culture on a glass microscopic slide. The film was allowed to air dry and then was heat fixed. The film was covered with crystal violet stain (0.1 g of crystal violet per 100 ml of H$_2$O) and warmed until steam appeared. The crystal violet was removed with 20% (wt/vol) aqueous copper sulfate solution (CuSO$_4$, 5H$_2$O; Fisher Scientific), blotted dry, the same covered in oil, a coverslip placed on top of the oil, and examined by light microscopy.

Biostatistics

To determine if a factor was characteristic of isolates from sick or healthy birds, the percent positive for each factor in each group was compared using a Z test of proportions (Maxwell, A. E., Analyzing Qualitative Data (Methuen Co., London (1961)). Also, the correlation of cvaC with traT- and iss sequences was calculated for the isolates from sick and healthy birds using the Pearson Product Moment Correlation (Maxwell, A. E., *Analyzing Qualitative Data*, Methuen Co., London (1961)).

Results

Hybridization Studies

Colony blot hybridization procedures were performed on all test and control isolates with each probe. None of the non-*E. coli* strains were detected by any of the prepared probes. Total DNA "dot" blots were found to yield unambiguous results, although the hybridization results were occasionally unclear, for example, false positives or false negatives obtained with the control organisms. The following results were obtained from either unambiguous colony blots or from "dot" blots.

It was observed that there was no significant difference in the distribution of traT, cvaC, or ompA sequences between the isolates from sick poultry and healthy poultry. All *E. coli* isolates contained ompA sequences. There was, however, a highly significant difference in the distribution of iss sequences in the isolates of sick poultry and healthy poultry, (p<0.000000001) as the isolates from sick poultry were much more likely to contain iss sequences than were the isolates from healthy poultry as shown in Table 6.

TABLE 6

| Gene | % isolates detected with gene | | Z | Probability of Z |
| --- | --- | --- | --- | --- |
|  | Sick Birds | Healthy Birds |  |  |
| cvaC | 66.66 | 58.9 | 1.12 | 0.26 |
| traT | 72.7 | 73.33 | 0.34 | 0.73 |
| iss | 76.33 | 23.2 | 6.69 | 0.000000001 |
| capsule | 1.9 | 8.9 | 2.57 | 0.01 |

Few encapsulated *E. coli* isolates were detected, and statistical analysis indicated that *E. coli* isolates from healthy poultry were more likely to be encapsulated than were the *E. coli* isolates from sick poultry (p<0.01, see Table 6).

Correlations between the occurrence of related sequences within the isolates from healthy or sick poultry were also determined for genes reportedly linked together on ColV plasmids (Waters et al., *Microbiol. Rev.*, 55:437–450 (1991)). For example, the occurrence of cvaC-related sequences for the *E. coli* isolates from healthy and sick poultry was not significantly correlated with the occurrence of iss-or traT-related sequences.

Approximately 23% of the non-disease-associated avian *E. coli* isolates examined contained iss-related sequences. It appears the iss isolates of healthy poultry are capable of causing disease, or that the isolates do not express the Iss protein or export the Iss polypeptide to the outer membrane where it is active in protection of the bacterium against host complement.

Detection of Iss on the Surface of Avian *E. coli* Isolates

Several methods are available to determine if an *E. coli* isolate expresses Iss. A preferred method indicates the presence of Iss on the outer membrane of the host bacterium where Iss can exert its anti-complement effect. Probing RNA using Northern blotting techniques provides evidence of iss transcription, but not translation or presence of Iss in the outer membrane. ELISAs to detect Iss in bacterial lysates are easy to perform and indicate the presence of Iss, but are not useful in determining whether ISS is present on the bacterial outer membrane. Assays useful to determine the location of Iss include fluorescent-antibody techniques or flow cytometry. Preferably, flow cytometry is employed to detect the location of Iss protein due to the accuracy and quantitative nature of the data obtained by this method.

To prepare samples for analysis by flow cytometry, bacteria are grown in Brain Heart Infusion (BHI) broth for 18 hours at 37° C. Bacteria are then washed and resuspended in buffer. Monoclonal antibodies specific for Iss are added to each bacterial suspension and allowed to incubate for 30 minutes. Suspensions are pelleted, washed thoroughly, and incubated with FITC-labeled, goat anti-mouse Ig conjugated antibody for 30 minutes at 0° C. After incubation, suspensions are pelleted, washed thoroughly, fixed with paraformaldehyde, and analyzed by flow cytometry using a FALSCalibur (Becton Dickinson, San Jose, Calif.) (Otten et al., *Flow Cytometry Analysis Using the Becton Dickinson FACScan*, John Wiley & Sons, New York, pp. 5.4.1–5.4.19 (1992)).

What is claimed is:

1. An isolated nucleic acid molecule comprising a nucleic acid sequence that encodes an *E. coli* Iss polypeptide wherein the nucleic acid molecule is isolated from *E. coli* obtained from a bird.

2. The nucleic acid molecule of claim 1 wherein the nucleic acid sequence comprises SEQ ID NO. 1.

3. The nucleic acid molecule of claim 1 wherein the nucleic acid sequence encodes a polypeptide having an amino acid sequence comprising SEQ ID NO. 2.

4. The nucleic acid molecule of claim 1 wherein the nucleic acid sequence is operably linked to a promoter functional in a host cell so as to form an expression vector.

5. An expression vector comprising the nucleic acid molecule of claim 1 further comprising control sequences recognized by a host cell transformed with the nucleic acid.

6. A method of using a nucleic acid molecule encoding an *E. coli* Iss polypeptide, the method comprising expressing the nucleic acid molecule of claim 1 in a cultured host cell stably transformed with a vector comprising the nucleic acid sequence operably linked to control sequences recognized by the host cell.

7. The method of claim 6 which further comprises recovering the polypeptide from the host cell.

8. The method of claim 6 wherein the nucleic acid molecule comprises SEQ ID NO. 1.

9. The method of claim 6 wherein the polypeptide has an amino acid sequence comprising SEQ ID NO. 2.

10. A method for producing a recombinant *E. coli* Iss polypeptide comprising:
    (a) providing an expression vector that comprises a nucleic acid sequence according to claim 1 operably linked to control sequences recognized by a host cell;
    (b) transforming the host cell with the vector; and
    (c) culturing the resultant transformed cell under conditions that allow expression of the recombinant polypeptide encoded by the nucleic acid sequence.

11. A method according to claim 10 wherein the host cell is prokaryotic.

12. A method according to claim 11 wherein the prokaryotic host cell is a gram negative or gram positive organism.

13. A method according to claim 11 wherein the host cell is *E. coli*.

14. A method according to claim 10 wherein the host cell is eukaryotic.

15. The isolated nucleic acid molecule of claim 1 wherein the bird is suspected of being exposed to, a carrier of, or afflicted with a septicemic disease.

16. The isolated nucleic acid molecule of claim 1 wherein the presence of the nucleic acid molecule is associated with a septicemic disease in the bird.

17. The nucleic acid molecule of claim 1 wherein the nucleic acid sequence comprises SEQ ID NO: 22.

18. The method of claim 6 wherein the nucleic acid molecule comprises SEQ ID NO: 22.

19. The method of claim 10 wherein the nucleic acid sequence comprises SEQ ID NO: 22.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 760 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GTGGCGAAAA CTAGTAAAAC AGCAACCCGA ACCACTTGAT GTGCATCGTT TTTGATTATT      60

CCCGTATACT CTTGCAGAAG GAGTTCTCCG TCGGGCTACT GTCATGGTTA ATGCGGGGAA     120

TATGGCGACA ATACAACACA CCTAAAAGAG TAATGGACAG ATGAAGCGGT TTATTCATTT     180

CCCATGATTC TGAGTACCTA CCAAGTCTGA GTAACCACTT TTATACTTTT AATTTTCGTT     240

CATTTAGCTA TCGTTTAATT ATTATCACAT AGGATTCTGC CGTTTTTAAC AATGCAGGAT     300

AATAAGATGA AAAAAATGTT ATTTTCTGCC GCTCTGGCAA TGCTTATTAC AGGATGTGCT     360
```

-continued

```
CAACAAACGT TTACTGTTGG AAACAAACCG ACAGCAGTAA CACCAAAGGA AACCATCACT      420

CATCATTTCT TCGTTTCGGG AATTGGACAA GAGAAAACTG TTGATGCAGC CAAAATTTGT      480

GGCGGTGCAG AAAATGTTGT TAAAACAGAA ACTCAGCAAA CATTCGTAAA TGGATTGCTC      540

GGTTTTATCA CTTTTGGCAT CTATACTCCG CTGGAAGCCC GGGTATATTG CTCACAATAG      600

TTGCCCATCG ATATGGGGAG CTCATCTGCA CTGTTCATTA ATATACTTCT GGGCTCCCTA      660

CAGTTGTTTT TGCATAGTGA TAAGCCTCTC TCTGAGGGAG GAAATAATCC TGTTCAGCGA      720

TGTCTGCCAG TCGGGGGGCT GCATTATCCA CCCCGAGGCG                            760
```

(2) INFORMATION FOR SEQ ID NO:2:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gln Asp Asn Lys Met Lys Lys Met Leu Phe Ser Ala Ala Leu Ala
 1               5                  10                  15

Met Leu Ile Thr Gly Cys Ala Gln Gln Thr Phe Thr Val Gly Asn Lys
            20                  25                  30

Pro Thr Ala Val Thr Pro Lys Glu Thr Ile Thr His His Phe Phe Val
        35                  40                  45

Ser Gly Ile Gly Gln Glu Lys Thr Val Asp Ala Ala Lys Ile Cys Gly
    50                  55                  60

Gly Ala Glu Asn Val Val Lys Thr Glu Thr Gln Gln Thr Phe Val Asn
65                  70                  75                  80

Gly Leu Leu Gly Phe Ile Thr Phe Gly Ile Tyr Thr Pro Leu Glu Ala
                85                  90                  95

Arg Val Tyr Cys Ser Gln
                100
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

```
GTGGCGAAAA CTAGTAAAAC AGC                                              23
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

```
CGCCTCGGGG TGGATAA                                                     17
```

(2) INFORMATION FOR SEQ ID NO:5:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
ATGCAGGATA ATAAGATGAA AAAAATGTTA TTTTCTGCCG CTCTGGCAAT GCTTATTACA      60

GGATGTGCTC AACAAACGTT TACTGTTGGA AACAAACCGA CAGCAGTAAC ACCAAAGGAA     120

ACCATCACTC ATCATTTCTT CGTTTCCCCA ATTGGACAGA GAAAACTGTT GATGCAGCCA     180

AAATTTGTTG GCGGTGCAGA AAATGTTGTT AAAACAGAAA CTCAGCAAAC ATTCGTAAAT     240

GCATTGCCCG GTTTTATCAC TTTTGGCATC TATACTCCGC GGGAAACCCG TGTATATTGC     300

TCACAATAG                                                             309
```

(2) INFORMATION FOR SEQ ID NO:6:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
ATCGGGAATA ACACCATGAA AAAAATGCTA CTCGCTACTG CGCTGGCCCT GCTTATTACA      60

GGATGTGCTC AACAGACGTT TACTGTTCAA AACAAACCGG CAGCAGTAGC ACCAAAGGAA     120

ACCATCACCC ATCATTTCTT CGTTTCTGGA ATTGGGCAGA GAAAACTGT CGATGCAGCC      180

AAAATTTGTG GCGGCGCAGA AAATGTTGTT AAAACAGAAA CCCAGCAAAC ATTCGTAAAT     240

GGATTGCTCG GTTTTATTAC TTTAGGCATT TATACTCCGC TGGAAGCGCG TGTGTATTGC     300

TCACAATAA                                                             309
```

(2) INFORMATION FOR SEQ ID NO:7:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Gln Asp Asn Lys Met Lys Lys Met Leu Phe Ser Ala Ala Leu Ala
1               5                   10                  15

Met Leu Ile Thr Gly Cys Ala Gln Gln Thr Phe Thr Val Gly Asn Lys
            20                  25                  30

Pro Thr Ala Val Thr Pro Lys Glu Thr Ile Thr His His Phe Val
        35                  40                  45

Ser Pro Ile Gly Gln Arg Lys Leu Leu Met Gln Pro Lys Phe Val Gly
    50                  55                  60

Gly Ala Glu Asn Val Val Lys Thr Glu Thr Gln Gln Thr Phe Val Asn
65                  70                  75                  80

Ala Leu Pro Gly Phe Ile Thr Phe Gly Ile Tyr Thr Pro Arg Glu Thr
                85                  90                  95
```

```
Arg Val Tyr Cys Ser Gln
                100
```

(2) INFORMATION FOR SEQ ID NO:8:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Lys Lys Met Leu Leu Ala Thr Ala Leu Ala Leu Ile Thr Gly
1               5                  10                  15

Cys Ala Gln Gln Thr Phe Thr Val Gln Asn Lys Pro Ala Ala Val Ala
                20                  25                  30

Pro Lys Glu Thr Ile Thr His His Phe Phe Val Ser Gly Ile Gly Gln
            35                  40                  45

Lys Lys Thr Val Asp Ala Ala Lys Ile Cys Gly Gly Ala Glu Asn Val
50                  55                  60

Val Lys Thr Glu Thr Gln Gln Thr Phe Val Asn Gly Leu Leu Gly Phe
65                  70                  75                  80

Ile Thr Leu Gly Ile Tyr Thr Pro Leu Glu Ala Arg Val Tyr Cys Ser
                85                  90                  95

Gln
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

CTTGCGGAGG CTTGTCTGAG                                                20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

AGGCATTGCT GGGTAAGGAA                                                20

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

AAAGGGGATC CATGCAGGAT AATAAGATGA AAAA                                              34

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CACAGGGATC CCAAACGTTT ACTGTTGGAA ACAA                                              34

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

CGCCGGAATT CGCAGATGAG CTCCCCATAT C                                                 31

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

ATGCAGGATA ATAAGATGAA AAA                                                          23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

ATAGATGCCA AAAGTGATAA AAC                                                          23

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CACGACGTTG TAAAACGAC                                                               19

```
(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

GGATAACAAT TTCACACAGG                                              20

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

GGGCTGGCAA GCCACGTTTG GTG                                          23

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

CCGGGAGCTG CATGTGTCAG AGG                                          23

(2) INFORMATION FOR SEQ ID NO:20:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Leu Glu Val Leu Phe Gln Gly Pro Leu Gly Ser Met Gln Asp Asn Lys
1               5                   10                  15

Met Lys Lys Met Leu Phe Ser Ala Ala Leu Ala Met Leu Ile Thr Gly
                20                  25                  30

Cys Ala Gln Gln Thr Phe Thr Val Gly Asn Lys Pro Thr Ala Val Thr
            35                  40                  45

Pro Lys Glu Thr Ile Thr His His Phe Phe Val Ser Gly Ile Gly Gln
        50                  55                  60

Glu Lys Thr Val Asp Ala Ala Lys Ile Cys Gly Gly Ala Glu Asn Val
65                  70                  75                  80

Val Lys Thr Glu Thr Gln Gln Thr Phe Val Asn Gly Leu Leu Gly Phe
                85                  90                  95

Ile Thr Phe Gly Ile Tyr Thr Pro Leu Glu Ala Arg Val Tyr Cys Ser
            100                 105                 110

Gln
```

(2) INFORMATION FOR SEQ ID NO:21:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CTGGAAGTTC TGTTCCAGGG GCCCCTGGGA TCCATGCAGG ATAATAAGAT GAAAAAAATG      60

TTATTTTCTG CCGCTCTGGC AATGCTTATT ACAGGATGTG CTCAACAAAC GTTTACTGTT     120

GGAAACAAAC CGACAGCAGT AACACCAAAG GAAACCATCA CTCATCATTT CTTCGTTTCG     180

GGAATTGGAC AAGAGAAAAC TGTTGATGCA GCCAAAATTT GTGGCGGTGC AGAAAATGTT     240

GTTAAAACAG AAACTCAGCA AACATTCGTA AATGGATTGC TCGGTTTTAT CACTTTTGGC     300

ATCTATACTC CGCTGGAAGC CCGGGTATAT TGCTCACAAT AGTTGCCCAT CGATATGGGG     360

AGCTCATCTG CGAATTCC                                                   378
```

(2) INFORMATION FOR SEQ ID NO:22:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
ATGCAGGATA ATAAGATGAA AAAAATGTTA TTTTCTGCCG CTCTGGCAAT GCTTATTACA      60

GGATGTGCTC AACAAACGTT TACTGTTGGA AACAAACCGA CAGCAGTAAC ACCAAAGGAA     120

ACCATCACTC ATCATTTCTT CGTTTCGGGA ATTGGACAAG AGAAAACTGT TGATGCAGCC     180

AAAATTTGTG GCGGTGCAGA AAATGTTGTT AAAACAGAAA CTCAGCAAAC ATTCGTAAAT     240

GGATTGCTCG GTTTTATCAC TTTTGGCATC TATACTCCGC TGGAAGCCCG GGTATATTGC     300

TCACAATAG                                                             309
```